(12) United States Patent
Cannas et al.

(10) Patent No.: US 10,995,074 B2
(45) Date of Patent: May 4, 2021

(54) AMIDINE CATALYST FOR CURABLE COMPOSITIONS

(71) Applicant: SIKA TECHNOLOGY AG, Baar (CH)

(72) Inventors: Rita Cannas, Dübendorf (CH); Urs Burckhardt, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 35 days.

(21) Appl. No.: 16/463,579

(22) PCT Filed: Dec. 12, 2017

(86) PCT No.: PCT/EP2017/082395
§ 371 (c)(1),
(2) Date: May 23, 2019

(87) PCT Pub. No.: WO2018/114476
PCT Pub. Date: Jun. 28, 2018

(65) Prior Publication Data
US 2019/0276412 A1    Sep. 12, 2019

(30) Foreign Application Priority Data

Dec. 21, 2016 (EP) .................................... 16206023

(51) Int. Cl.
| | |
|---|---|
| *C07D 239/06* | (2006.01) |
| *C07D 239/26* | (2006.01) |
| *C08G 77/46* | (2006.01) |
| *C09D 183/12* | (2006.01) |
| *C09J 183/12* | (2006.01) |

(52) U.S. Cl.
CPC ......... *C07D 239/26* (2013.01); *C07D 239/06* (2013.01); *C08G 77/46* (2013.01); *C09D 183/12* (2013.01); *C09J 183/12* (2013.01)

(58) Field of Classification Search
CPC ..... C07D 239/06; C08L 83/06; C08L 101/10; C08L 75/04; C09J 201/10; C09D 175/04; C07F 7/18; C08K 5/17
See application file for complete search history.

(56) References Cited

U.S. PATENT DOCUMENTS

| | | | |
|---|---|---|---|
| 3,251,854 A | 5/1966 | Sims et al. | |
| 2009/0029888 A1* | 1/2009 | Ravichandran | C10M 141/08 508/362 |

FOREIGN PATENT DOCUMENTS

| | | |
|---|---|---|
| EP | 1985666 A1 | 10/2008 |
| WO | 2015/158859 A2 | 10/2015 |
| WO | 2015/158860 A1 | 10/2015 |
| WO | 2015/193208 A2 | 12/2015 |
| WO | 2016/166225 A1 | 10/2016 |

OTHER PUBLICATIONS

Jun. 25, 2019 International Preliminary Report on Patentability issued in International Patent Application No. PCT/EP2017/082395.
Feb. 27, 2018 International Search Report issued in International Patent Application No. PCT/EP2017/082395.

* cited by examiner

*Primary Examiner* — Kuo Liang Peng
(74) *Attorney, Agent, or Firm* — Oliff PLC

(57) ABSTRACT

An amidine containing at least one structural unit of the formula (I) and the use thereof as catalyst for the crosslinking of a functional compound, especially of a polymer having silane groups. The amidine is preparable in a simple process from readily available starting materials, is largely odorless at room temperature and is of low toxicity. It accelerates the crosslinking of functional compounds surprisingly efficiently and can be adjusted for optimal compatibility with different compositions via the radical to which the structural units of the formula (I) is bonded, which means that such compositions do not have a tendency to migration-related defects such as separation, exudation or substrate soiling.

15 Claims, No Drawings

AMIDINE CATALYST FOR CURABLE COMPOSITIONS

TECHNICAL FIELD

The invention relates to amidines and to the use thereof as catalyst for curable compositions, especially based on polymers having silane groups.

PRIOR ART

Curable compositions play a significant role in many industrial applications, for example as adhesives, sealants or coatings. The curing thereof is brought about by crosslinking reactions which proceed via reactive groups, for example silane groups, isocyanate groups or epoxy groups, wherein these react with themselves or a coreactant following a mixing operation or through heating or through contact with moisture, and hence form a polymeric network in the composition. Acceleration of such crosslinking reactions is frequently accomplished using catalysts. These are very often substances of toxicological concern which constitute a potential hazard to users and the environment, especially after the curing of the composition, if the catalyst or degradation products thereof are released by outgassing, migration or washing-out. Compositions curable at room temperature that are based on polymers having silane groups are confronted with this problem to a significant degree. Polymers having silane groups here are especially polyorganosiloxanes, which are commonly referred to as "silicones" or "silicone rubbers", and organic polymers having silane groups, which are also referred to as "silane-functional polymers", "silane-modified polymers" (SMP) or "silane-terminated polymers" (STP). The crosslinking thereof proceeds via the condensation of silanol groups to form siloxane bonds and is conventionally catalyzed by means of organotin compounds such as dialkyltin(IV) carboxylates in particular. These are notable for very high activity in relation to the silanol condensation and are very hydrolysis-resistant, but they are harmful to health and a severe water pollution hazard. They are often combined with further catalysts, mainly basic compounds, such as amines in particular, which particularly accelerate the preceding hydrolysis of the silane groups.

Because greater weight is being given to EHS aspects by professional organizations and users and because of stricter government regulation, there have been increased efforts for some time to replace organotin compounds with other catalysts of lower toxicity. For instance, organotitanates, -zirconates and -aluminates have been described as alternative metal catalysts. However, these usually have lower catalytic activity in relation to the silanol condensation and bring about much slower crosslinking. Because of their lack of hydrolysis stability, they can lose a large part of their activity in the course of storage of the composition as a result of residual moisture in the ingredients, which causes the curing to slow significantly or stop entirely.

A further known alternative to organotin compounds is highly basic nitrogen compounds from the class of the amidines and guanidines, which can be used in combination with the metal catalysts mentioned or else alone. However, many of the commonly used amidine and guanidine catalysts, such as, in particular, 1,8-diazabicyclo[5.4.0]undec-7-ene (DBU) or 1,1,3,3-tetramethylguanidine (TMG), are volatile and odorous substances that are likewise harmful to health and hazardous to the environment. Moreover, they have a tendency to migrate because of low compatibility with the composition and hence to cause separation, exudation or substrate soiling.

Further amidine catalysts are known from WO 2015/158859, WO 2015/158860, WO 2015/193208 and WO 2016/166336. However, these catalysts are still capable of improvement with regard to their catalytic activity and/or compatibility with different polymer systems.

SUMMARY OF THE INVENTION

It is therefore an object of the present invention to provide a catalyst which overcomes the disadvantages of the prior art and especially has low odor and low toxicity, has high catalytic activity for the crosslinking reaction of functional compounds and has good compatibility with curable compositions thereof.

This object is achieved by an amidine containing at least one structural unit of the formula (I) as described in claim 1. The amidine of the invention is largely odorless and of low toxicity. In spite of elevated molecular weight, it has surprisingly high catalytic activity for the crosslinking reaction of various functional compounds, especially compounds having silane groups and/or isocyanate groups, and brings about rapid curing of curable compositions thereof. The amidine is preparable in a surprisingly simple manner from readily obtainable raw materials, and it can be optimized with regard to its compatibility with different curable compositions via the radical to which the structural unit of the formula (I) is bonded, such that it has good miscibility therewith and shows barely any separation or migration either before or after curing.

Further aspects of the invention form the subject matter of further independent claims. Particularly preferred embodiments of the invention form the subject matter of the dependent claims.

WAYS OF EXECUTING THE INVENTION

The invention provides an amidine containing at least one structural unit of the formula (I)

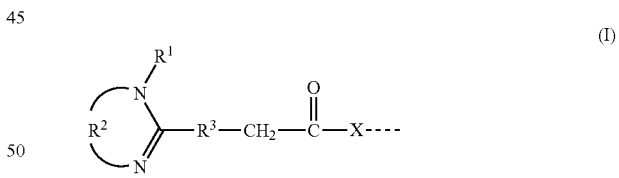

where
$R^1$ is a hydrogen radical or an alkyl, cycloalkyl or aralkyl radical optionally having unsaturated moieties, having 1 to 30 carbon atoms and optionally having a tertiary amino group,
$R^2$ is an optionally alkyl-substituted 1,2-ethylene or 1,3-propylene radical,
$R^3$ is an optionally alkyl-substituted 1,3-propylene or 1,4-butylene radical, and
X is O or $NR^4$ where $R^4$ is a hydrogen radical or is an alkyl, cycloalkyl or aralkyl radical having 1 to 8 carbon atoms.

A dotted line in the formulae in this document in each case represents the bond between a substituent and the corresponding molecular radical.

"Primary amino group" and "primary amine nitrogen" refer respectively to an amino group and the nitrogen atom thereof that is bonded to a single organic radical and bears two hydrogen atoms; "secondary amino group" and "secondary amine nitrogen" refer respectively to an amino group and the nitrogen atom thereof that is bonded to two organic radicals which may also together be part of a ring and bears one hydrogen atom; and "tertiary amino group" and "tertiary amine nitrogen" refer respectively to an amino group and the nitrogen atom thereof that is bonded to three organic radicals, two or three of which together may also be part of one or more rings, and does not bear any hydrogen atom.

"Functional compound" refers to a compound which cures with a suitable coreactant to give a polymeric structure and bears at least one reactive group, especially at least two reactive groups. Their reactive groups are typically electrophilic, whereas the coreactants are nucleophilic or bear nucleophilic groups.

A "curable" composition refers to one that can cure through crosslinking reactions of reactive groups present therein or attain a state of elevated mechanical strength.

"Siloxane radical" refers to a radical containing at least one siloxane bond Si—O—Si.

"Polysiloxane radical" or "polyorganosiloxane radical" refers to a siloxane radical containing multiple siloxane bonds in sequence, i.e. Si—(O—Si)$_s$ units with s=2 or more. An (O—Si) unit is referred to here as "siloxane unit". The siloxane units here are additionally substituted by organic radicals, especially methyl and/or phenyl groups.

The term "silane group" refers to a silyl group which is bonded to an organic radical or to a polysiloxane radical and has one to three, especially two or three, hydrolyzable substituents on the silicon atom. Particularly commonly used hydrolyzable substituents are alkoxy radicals. These silane groups are also referred to as "alkoxysilane groups". Silane groups may also be in partly or fully hydrolyzed form.

"Silane" refers both to organoalkoxysilanes bearing one to three organic substituents on each alkoxysilane group and tetraalkoxysilanes. Silanes that bear one or more hydroxyl, isocyanato, amino or mercapto groups in addition to the silane group on an organic radical are referred to as "hydroxysilane", "isocyanatosilane", "aminosilane" and "mercaptosilane" respectively.

The term "organic polymer" encompasses a collective of macromolecules that are chemically homogeneous but differ in relation to degree of polymerization, molar mass and chain length, which has been prepared by a poly reaction (polymerization, polyaddition, polycondensation) and has a majority of carbon atoms in the polymer backbone, and reaction products of such a collective of macromolecules. Polymers having a polyorganosiloxane backbone (commonly referred to as "silicones") are not organic polymers in the context of the present document.

The term "polyether having silane groups" also encompasses organic polymers which have silane groups and, in addition to polyether units, may also contain urethane groups, urea groups or thiourethane groups. Such polyethers having silane groups may also be referred to as "polyurethanes having silane groups". "Molecular weight" refers to the molar mass (in g/mol) of a molecule. "Average molecular weight" is the number average $M_n$ of a polydisperse mixture of oligomeric or polymeric molecules, which is typically determined by means of gel permeation chromatography (GPC) against polystyrene as standard. "Storage-stable" or "storable" refers to a substance or composition if it can be stored at room temperature in a suitable container over a prolonged period, typically from at least 3 months up to 6 months or more, without any change in its application or use properties, especially in the viscosity and crosslinking rate, to an extent relevant for the use thereof, as a result of the storage. "Room temperature" refers to a temperature of about 23° C.

The structural unit of the formula (I) may also be in protonated form. It may likewise be in complexed form, especially with cations of zinc, iron or molybdenum.

Amidines containing at least one structural unit of the formula (I) having siloxane units are of particularly good compatibility with polyorganosiloxane polymers and hence particularly suitable as catalyst for such functional compounds or curable compositions.

Amidines containing at least one structural unit of the formula (I) having polyoxyalkylene units are of particularly good compatibility with polyether polymers and hence particularly suitable as catalyst for such functional compounds or curable compositions.

Amidines containing at least one structural unit of the formula (I) having a tertiary amino group are particularly active as catalyst for compositions having isocyanate groups and/or epoxy groups.

Preferably, $R^1$ is a hydrogen radical or an alkyl or cycloalkyl radical optionally having unsaturated moieties, having 1 to 18 carbon atoms and optionally having a tertiary amino group. Amidines having such structural units are particularly easily obtainable.

More preferably, $R^1$ is selected from the group consisting of methyl, ethyl, propyl, butyl, cyclohexyl, 2-ethylhexyl, n-decyl, lauryl, cocoalkyl, oleyl, soyaalkyl, tallowalkyl and 3-(N,N-dimethylamino)propyl. Amidines having these structural units are very particularly easily obtainable.

Among these, preference is given to 3-(N,N-dimethylamino)propyl. Amidines having this structural unit show particularly high catalytic activity.

Preferably, $R^2$ is an optionally alkyl-substituted 1,3-propylene radical. Amidines having such a structural unit show particularly high catalytic activity.

Most preferably, $R^2$ is 1,3-propylene.

Preferably, $R^3$ is an unsubstituted 1,3-propylene radical or 1,4-butylene radical. Most preferably, $R^3$ is 1,3-propylene. Amidines having such structural units are particularly easily obtainable and particularly catalytically active.

Preferably, X is $NR^4$. Amidines having such structural units are particularly stable and can be varied particularly efficiently via the radical to which the structural unit is bonded.

Preferably, $R^4$ is a hydrogen radical or an alkyl radical having 1 to 8, especially 1 to 4, carbon atoms.

The amidine containing at least one structural unit of the formula (I) preferably has the formula (II)

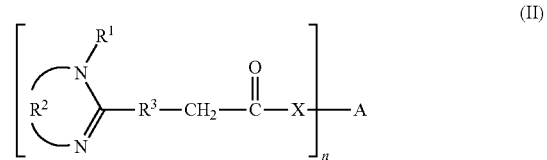

where n is 1 or 2 or 3,

A is an n-valent radical which has a molecular weight in the range from 28 to 5'000 g/mol and is bonded via carbon atoms, and $R^1$, $R^2$, $R^3$ and X have the definitions already given.

Preferably, A is a monovalent hydrocarbyl radical which has 1 to 30 carbon atoms and optionally contains ether oxygen or tertiary amine nitrogen or siloxane units. Such an amidine is of particularly low viscosity and easily processible.

Such a monovalent A radical is especially selected from the group consisting of methyl, ethyl, 1-propyl, 2-propyl, n-butyl, 2-butyl, isobutyl, tert-butyl, n-pentyl, 2-pentyl, isopentyl, n-hexyl, n-octyl, 2-ethylhexyl, n-decyl, lauryl, cyclohexyl, benzyl, 2-methoxyethyl, 3-methoxypropyl, 3-(N,N-dimethylamino)propyl and methylpolyoxyalkylene with oxyethylene and/or 1,2-oxypropylene units and an average molecular weight in the range from 180 to 600 g/mol.

Further preferably, A is a di- or trivalent hydrocarbyl radical which has 2 to 50 carbon atoms and optionally contains ether oxygen or tertiary amine nitrogen or siloxane units. Such an amidine is of particularly good compatibility with curable compositions and has a particularly low tendency to migration. Preferably, X here is $NR^4$ and $R^4$ here is preferably a hydrogen radical or a methyl radical.

Such a di- or trivalent A radical is especially selected from the group consisting of 1,2-ethylene, 1,2-propylene, 1,3-propylene, 1,4-butylene, 1,3-pentylene, 1,5-pentylene, 2,2-dimethyl-1,3-propylene, 2-methyl-1,5-pentylene, 1,6-hexylene, 2,2(4),4-trimethyl-1,6-hexamethylene, 1,8-octylene, 1,10-decylene, 1,12-dodecylene, (1,5,5-trimethylcyclohexan-1-yl)methane-1,3, 1,3-cyclohexylenebis(methylene), 1,4-cyclohexylenebis(methylene), 1,3-phenylenebis(methylene), 2- and/or 4-methyl-1,3-cyclohexylene, N-methyl-4-aza-1,7-heptylene, 3-oxa-1,5-pentylene, 3,6-dioxa-1,8-octylene, 4,7-dioxa-1,10-decylene, α,ω-polyoxypropylene having an average molecular weight in the range from 170 to 2'000 g/mol, trimethylolpropane- or glycerol-started tris(w-polyoxypropylene) having an average molecular weight in the range from 330 to 5'000 g/mol, bis(3-propyl)-1,1,3,3-tetramethyldisiloxane and α,ω-(1,3-propylene)polydimethylsiloxane having an average molecular weight in the range from 350 to 2'000 g/mol.

Among these, preference is given to 1,2-ethylene, 1,2-propylene, 1,3-propylene, 1,4-butylene, 1,3-pentylene, 1,5-pentylene, 2,2-dimethyl-1,3-propylene, 2-methyl-1,5-pentylene, 1,6-hexylene, 2,2(4),4-trimethyl-1,6-hexamethylene, 1,8-octylene, 1,10-decylene, 1,12-dodecylene, (1,5,5-trimethylcyclohexan-1-yl)methane-1,3, 1,3-cyclohexylenebis(methylene), 1,4-cyclohexylenebis(m ethylene), 1,3-phenylenebis(methylene), 2- and/or 4-methyl-1,3-cyclohexylene or N-methyl-4-aza-1,7-heptylene. These amidines of the formula (II) are particularly catalytically active.

Among these, preference is further given to 3-oxa-1,5-pentylene, 3,6-dioxa-1,8-octylene, 4,7-dioxa-1,10-decylene, α,ω-polyoxypropylene having an average molecular weight in the range from 170 to 2'000 g/mol or trimethylolpropane- or glycerol-started tris(w-polyoxypropylene) having an average molecular weight in the range from 330 to 5'000 g/mol. These amidines of the formula (II) are of particularly good compatibility with curable compositions based on polyether polymers, especially polyethers having silane groups.

Among these, preference is further given to bis(3-propyl)-1,1,3,3-tetramethyldisiloxane or α,ω-(1,3-propylene)polydimethylsiloxane having an average molecular weight in the range from 350 to 2'000 g/mol. These amidines of the formula (II) are of particularly good compatibility with curable compositions based on polyorganosiloxane polymers.

The invention further provides a process for preparing the amidine of the formula (II) by reacting at least one amine A1 of the formula (III) with a compound of the formula (IV) with removal of water

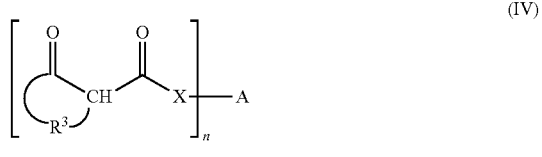

where $R^1$, $R^2$, $R^3$, X, A and n have the definitions already given.

The process is performable in a surprisingly rapid and simple manner, especially without the use of auxiliaries and without requiring complex purification of the reaction product, and proceeds from commercially available, inexpensive starting materials. What is particularly surprising here is the fact that the cyclic compound of the formula (IV) gives rise to a cyclic amidine of the formula (II) in a simple manner with ring opening and ring reclosure under mild conditions.

The process is preferably conducted at a temperature in the range from 20 to 120° C., more preferably 30 to 80° C., especially 40 to 60° C., where the reactants may be mixed with one another in any sequence. The water of reaction is removed after the reaction, preferably by applying reduced pressure and/or by azeotropic distillation with an organic solvent. Volatile constituents that remain after the reaction are preferably distilled off, especially under reduced pressure. Such a reaction product can be used as catalyst without further workup or purification.

The use of a compound of the formula (IV) in which X is $NR^4$ has the advantage that the reaction with the amine A1 of the formula (III) forms a lower level of by-products and the reaction product formed thus has a particularly high content of amidine of the formula (II).

Suitable amines A1 of the formula (III) are especially ethane-1,2-diamine, N-methylethane-1,2-diamine, N-ethylethane-1,2-diamine, N-propylethane-1,2-diamine, N-isopropylethane-1,2-diamine, N-butylethane-1,2-diamine, N-cyclohexylethane-1,2-diamine, N-(2-ethylhexyl)ethane-1,2-diamine, propane-1,2-diamine, N-methylpropane-1,2-diamine, N-ethylpropane-1,2-diamine, N-benzylpropane-1,2-diamine, 2-methylpropane-1,2-diamine, propane-1,3-diamine, N-methylpropane-1,3-diamine, N-ethylpropane-1,3-diamine, N-propylpropane-1,3-diamine, N-isopropylpropane-1,3-diamine, N-butylpropane-1,3-diamine, N-cyclohexylpropane-1,3-diamine, N-(2-ethylhexyl)propane-1,3-diamine, N-laurylpropane-1,3-diamine, N-cocoalkylpropane-1,3-diamine, N-oleylpropane-1,3-diamine, N-soyaalkylpropane-1,3-diamine, N-tallowalkylpropane-1,3-diamine, 3-(3-(dimethylamino)propylamino)propylamine, 2,2-dimethylpropane-1,3-diamine, butane-1,3-diamine, pentane-1,3-diamine (DAMP), N-methylpentane-1,3-diamine, 1,2-diaminocyclohexane, 1,3-diaminocyclohexane or 2(4)-methyl-1,3-diaminocyclohexane.

Preferred amines A1 of the formula (III) are ethane-1,2-diamine, N-methylethane-1,2-diamine, N-ethylethane-1,2-diamine, N-propylethane-1,2-diamine, N-isopropylethane-1,2-diamine, N-butylethane-1,2-diamine, N-cyclohexylethane-1,2-diamine, propane-1,2-diamine, propane-1,3-diamine, N-methylpropane-1,3-diamine, N-ethylpropane-1,3-diamine, N-propylpropane-1,3-diamine, N-isopropylpropane-1,3-diamine, N-butylpropane-1,3-diamine, N-cyclohexylpropane-1,3-diamine, N-(2-ethylhexyl)propane-1,3-diamine, N-laurylpropane-1,3-diamine, N-cocoalkylpropane-1,3-diamine, N-oleylpropane-1,3-diamine, N-soyaalkylpropane-1,3-diamine, N-tallowalkylpropane-1,3-diamine, 3-(3-(dimethylamino)propylamino)propylamine, 2,2-dimethylpropane-1,3-diamine, butane-1,3-diamine or pentane-1,3-diamine (DAMP).

Particularly preferred amines A1 of the formula (III) are propane-1,3-diamine, N-methylpropane-1,3-diamine, N-ethylpropane-1,3-diamine, N-butylpropane-1,3-diamine, N-cyclohexylpropane-1,3-diamine, N-(2-ethylhexyl)propane-1,3-diamine, N-decylpropane-1,3-diamine, N-laurylpropane-1,3-diamine or 3-(3-(dimethylamino)propylamino)propylamine.

Suitable compounds of the formula (IV) are those with X=O. Such cyclic 1,3-keto esters are especially reaction products from the Dieckmann condensation of adipic or pimelic esters. Particularly suitable examples are methyl 2-oxocyclopentanecarboxylate, ethyl 2-oxocyclopentanecarboxylate, methyl 2-oxocyclohexanecarboxylate, ethyl 2-oxocyclohexanecarboxylate or analogs thereof with higher alcohols, or ethylene 1,2-bis(2-oxocyclopentanoate) or analogs of longer-chain diols or polyalkylene oxide polyols.

Preferred compounds of the formula (IV) are those with X=$NR^4$. Such mono- or polyfunctional cyclic 1,3-keto amides are obtainable either directly from the Dieckmann condensation of corresponding adipamides or pimelamides, or they can be prepared by reacting the above-described cyclic 1,3-keto esters with at least one amine A2 of the formula A-$(NHR^4)_n$ with release of the corresponding alcohol.

Preference is given to using, for the process described, a compound of the formula (IV) with X=$NR^4$ which has been obtained beforehand by reacting at least one amine A2 of the formula A-$(NHR^4)_n$ with a compound of the formula (IV) with X=O with removal of the corresponding alcohol. A, $R^4$ and n have the definitions already given.

By this preparation, the structure of the amidine of the formula (II) can be optimized in a particularly simple manner with regard to its compatibility with different curable compositions.

The compound of the formula (IV) with X=O for this prior reaction is preferably selected from the group consisting of methyl 2-oxocyclopentanecarboxylate, ethyl 2-oxocyclopentanecarboxylate, methyl 2-oxocyclohexanecarboxylate and ethyl 2-oxocyclohexanecarboxylate.

The amine A2 of the formula A-$(NHR^4)_n$ is preferably selected from the group consisting of dimethylamine, diethylamine, dipropylamine, N-ethyl-N-propylamine, diisopropylamine, N-methyl-N-isopropylamine, 1-butylamine, dibutylamine, 2-butylamine, isobutylamine, tert-butylamine, N-methyl-N-butylamine, n-pentylamine, 2-pentylamine, isopentylamine, n-hexylamine, n-octylamine, 2-ethylhexylamine, di(2-ethylhexyl)amine, n-decylamine, laurylamine, cocoalkylamine, oleylamine, soyaalkylamine, tallowalkylamine, cyclohexylamine, dicyclohexylamine, N-methyl-N-cyclohexylamine, benzylamine, N-methyl-N-benzylamine, 2-methoxyethylamine, 3-methoxypropylamine, 3-(N,N-dimethylamino)propylamine, methylpolyoxyalkyleneamine having oxyethylene and/or 1,2-oxypropylene units and an average molecular weight in the range from 180 to 600 g/mol, especially Jeffamine® M-600 (from Huntsman), ethane-1,2-diamine, propane-1,2-diamine, propane-1,3-diamine, butane-1,4-diamine, pentane-1,3-diamine, pentane-1,5-diamine, 2,2-dimethylpropane-1,3-diamine, 2-methylpentane-1,5-diamine, hexane-1,6-diamine, 2,2(4),4-trimethylhexane-1,6-diamine, octane-1,8-diamine, decane-1,10-diamine, dodecane-1,12-diamine, N-methylethane-1,2-diamine, N-ethylethane-1,2-diamine, N-propylethane-1,2-diamine, N-isopropylethane-1,2-diamine, N-butylethane-1,2-diamine, N-cyclohexylethane-1,2-diamine, N-methylpropane-1,3-diamine, N-ethylpropane-1,3-diamine, N-propylpropane-1,3-diamine, N-isopropylpropane-1,3-diamine, N-butylpropane-1,3-diamine, N-cyclohexylpropane-1,3-diamine, N-(2-ethylhexyl)propane-1,3-diamine, N-laurylpropane-1,3-diamine, N-cocoalkylpropane-1,3-diamine, N-oleylpropane-1,3-diamine, N-soyaalkylpropane-1,3-diamine, N-tallowalkylpropane-1,3-diamine, 1-amino-3-aminomethyl-3,5,5-trimethylcyclohexane (isophoronediamine or IPDA), 1,3-bis(aminomethyl)cyclohexane, 1,4-bis(aminomethyl)cyclohexane, 1,3-bis(aminomethyl)benzene, 2- and/or 4-methyl-1,3-diaminocyclohexane, N,N-bis(3-aminopropyl)methylamine, bis(2-aminoethyl) ether, 3,6-dioxaoctane-1,8-diamine, 4,7-dioxadecane-1,10-diamine, 4,7-dioxadecane-2,9-diamine, 4,9-dioxadodecane-1,12-diamine, α,ω-polyoxypropylenediamines having an average molecular weight in the range from 200 to 2'000 g/mol, especially Jeffamines® D-230, D-400, D-2000, SD-231, SD-401 and SD-2001 (from Huntsman), trimethylolpropane- or glycerol-started tris(ω-aminopolyoxypropylene) having an average molecular weight in the range from 330 to 5'000 g/mol, especially Jeffamines® T-403, T-3000, T-5000 and HBZ-404 (from Huntsman), bis(3-aminopropyl)-1,1,3,3-tetramethyldisiloxane and α,ω-(3-aminopropyl)polydimethylsiloxane having an average molecular weight in the range from 350 to 2'000 g/mol.

Preference is likewise given to a process for preparing an amidine of the formula (II) in which n is 2 and X is $NR^4$ by reacting two moles of amidine of the formula (II) with n=1 and X=O with one mole of amine A2 having two primary or secondary amino groups.

Particularly preferred compounds of the formula (IV) are N-butyl-(2-oxocyclopentyl)carbonamide, N-butyl-(2-oxocyclohexyl)carbonamide, N-hexyl-(2-oxocyclopentyl)carbonamide, N-hexyl-(2-oxocyclohexyl)carbonamide, N,N-diethyl-(2-oxocyclopentyl)carbonamide, N,N-diethyl-(2-oxocyclohexyl)carbonamide, N,N-dibutyl-(2-oxocyclopentyl)carbonamide, N,N-dibutyl-(2-oxocyclohexyl)carbonamide, N-methyl-N-butyl-(2-oxocyclopentyl)carbonamide, N-methyl-N-butyl-(2-oxocyclohexyl)carbonamide, N-methyl-N-benzyl-(2-oxocyclopentyl)carbonamide, N-methyl-N-benzyl-(2-oxocyclohexyl)carbonamide, N-(2-ethylhexyl)-(2-oxocyclopentyl)carbonamide, N-(2-ethylhexyl)-(2-oxocyclohexyl)carbonamide, N-benzyl-(2-oxocyclopentyl)carbonamide, N-benzyl-(2-oxocyclohexyl)carbonamide, N-cyclohexyl-(2-oxocyclopentyl)carbonamide, N-cyclohexyl-(2-oxocyclohexyl)carbonamide, N-(3-dimethylaminopropyl)-(2-oxocyclopentyl)carbonamide, N-(3-dimethylaminopropyl)-(2-oxocyclohexyl)carbonamide, N-(2-methoxyethyl)-(2-oxocyclopentyl)carbonamide, N-(2-methoxyethyl)-(2-oxocyclohexyl)carbonamide or analogous amides of alkylpolyoxyalkyleneamines with oxyethylene and/or 1,2-oxypropylene units and an average molecular weight in the range from about 180 to 600 g/mol, or di- or triamides such as, in particular, N,N'-ethylenebis((2-oxocyclopentyl)carbonamide), N,N'-ethylenebis((2-oxocyclohexyl)carbonamide) or analogous di- or triamides of higher di- or triamines such as the aforementioned amines of the formula A-$(NHR^4)_n$ with n=2 or 3.

The invention further provides for the use of the amidine containing at least one structural unit of the formula (I) as catalyst for the crosslinking of a functional compound. The amidine here catalyzes the crosslinking reaction of the reactive groups or the curing of the functional compound and curable compositions thereof.

Preferred reactive groups of the functional compound are silane groups, isocyanate groups, epoxy groups or cyanate ester groups.

Suitable functional compounds are especially
silanes,
polymers having silane groups,
polyisocyanates,
polymers having isocyanate groups, especially polyurethane polymers having isocyanate groups,
compounds having glycidoxy groups, especially epoxy resins,
cyanate ester resins, or
polymers having various reactive groups, especially compounds or polymers having isocyanate and silane groups or having isocyanate and epoxy groups.

The functional compound is preferably a silane, a polymer having silane groups, a polyisocyanate or a polyurethane polymer having isocyanate groups.

Suitable polyisocyanates are especially monomeric diisocyanates, or oligomers or polymers or derivatives of monomeric diisocyanates, or any mixtures thereof.

Suitable monomeric diisocyanates are especially tolylene 2,4- or 2,6-diisocyanate or any mixtures of these isomers (TDI), diphenylmethane 4,4'-, 2,4'- or 2,2'-diisocyanate or any mixtures of these isomers (MDI), mixtures of MDI and MDI homologs (polymeric MDI or PMDI), phenylene 1,3- or 1,4-diisocyanate, 2,3,5,6-tetramethyl-1,4-diisocyanatobenzene, naphthalene 1,5-diisocyanate (NDI), 3,3'-dimethyl-4,4'-diisocyanatodiphenyl (TODI), dianisidine diisocyanate (DADI), tetramethylene 1,4-diisocyanate, 2-methylpentamethylene 1,5-diisocyanate, hexamethylene 1,6-diisocyanate (HDI), 2,2(4),4-trimethylhexamethylene 1,6-diisocyanate (TMDI), decamethylene 1,10-diisocyanate, dodecamethylene 1,12-diisocyanate, lysine or lysine ester diisocyanate, cyclohexane 1,3- or 1,4-diisocyanate, 1-methyl-2,4- or -2,6-diisocyanatocyclohexane or any desired mixtures of these isomers (HTDI or $H_6$TDI), 1-isocyanato-3,3,5-trimethyl-5-isocyanatomethylcyclohexane (isophorone diisocyanate or IPDI), perhydro(diphenylmethane 2,4'- or 4,4'-diisocyanate) (HMDI or $H_{12}$MDI), 1,4-diisocyanato-2,2,6-trimethylcyclohexane (TMCDI), 1,3- or 1,4-bis(isocyanatomethyl)cyclohexane, m- or p-xylylene diisocyanate (m- or p-XDI), m- or p-tetramethylxylylene 1,3- or 1,4-diisocyanate (m- or p-TMXDI) or bis(1-isocyanato-1-methylethyl)naphthalene.

Among these, preference is given to MDI, TDI, IPDI or HDI.

Suitable oligomers, polymers or derivatives of monomeric diisocyanates are especially derived from MDI, TDI, HDI or IPDI.

Particularly preferred polyisocyanates are forms of MDI that are liquid at room temperature and have a high content of diphenylmethane 4,4'-diisocyanate. What is called "liquid MDI" is especially either diphenylmethane 4,4'-diisocyanate liquefied by partial chemical modification—especially carbodiimidization or uretonimine formation—or a mixture of diphenylmethane 4,4'-diisocyanate with other MDI isomers (2,4'-diphenylmethane diisocyanate and/or 2,2'-diphenylmethane diisocyanate) or MDI oligomers or MDI homologs that has been brought about selectively by blending or results from the production process.

Suitable polyurethane polymers having isocyanate groups are especially obtained from the reaction of at least one polyol with a superstoichiometric amount of at least one polyisocyanate, especially a diisocyanate. The reaction is preferably conducted with exclusion of moisture at a temperature in the range from 50 to 160° C., optionally in the presence of suitable catalysts. The excess of polyisocyanate is preferably chosen so as to leave, in the polyurethane polymer after the conversion of all hydroxyl groups, a content of free isocyanate groups in the range from 1% to 30% by weight, preferably 1.5% to 25% by weight, more preferably 2% to 20% by weight. The polyurethane polymer can optionally be prepared with additional use of plasticizers or solvents, in which case the plasticizers or solvents used do not contain any groups reactive toward isocyanates.

Diisocyanates suitable for this purpose are especially MDI, TDI, PMDI, HDI, IPDI, $H_{12}$MDI, or oligomers or derivatives of these diisocyanates.

Polyols suitable for this purpose are especially polyether polyols, preferably polyoxyalkylene polyols, which are polymerization products of ethylene oxide or 1,2-propylene oxide or 1,2- or 2,3-butylene oxide or oxetane or tetrahydrofuran or mixtures thereof, possibly polymerized with the aid of a starter molecule having two or more active hydrogen atoms; polyester polyols, preferably products from the polycondensation of diols or triols with lactones or dicarboxylic acids or esters or anhydrides thereof; polycarbonate polyols; OH-terminal block copolymers having at least two different blocks having polyether, polyester or polycarbonate units; polyacrylate polyols or polymethacrylate polyols; polyhydroxy-functional fats or oils, especially natural fats or oils; or polyhydrocarbon polyols, for example polyhydroxy-functional polyolefins, especially polybutadienepolyols.

Also especially suitable are mixtures of the polyols mentioned.

Especially suitable are diols or triols or mixtures thereof.

The polyurethane polymer having isocyanate groups preferably has an average molecular weight in the range from 350 to 30'000 g/mol, especially 1'000 to 15'000 g/mol.

Particularly preferred functional compounds are silanes and or polymers having silane groups.

The amidine containing at least one structural unit of the formula (I) has a strong catalytic effect on the hydrolysis and condensation reactions of silane groups. Silanes and polymers having silane groups therefore cure rapidly even with a relatively small amount of this catalyst.

Suitable silanes are especially tetramethoxysilane, tetraethoxysilane, methyltrimethoxysilane, ethyltrimethoxysilane, propyltrimethoxysilane, octyltrimethoxysilane, isooctyltrimethoxysilane, vinyltrimethoxysilane, phenyltrimethoxysilane, methyltriethoxysilane, octyltriethoxysilane, isooctyltriethoxysilane, vinyltriethoxysilane, phenyltriethoxysilane, aminosilanes such as, in particular, 3-aminopropyltrimethoxysilane, 3-aminopropyldimethoxymethylsilane, N-(2-aminoethyl)-3-aminopropyltrimethoxysilane, N-(2-aminoethyl)-3-aminopropyldimethoxymethylsilane, N-(2-aminoethyl)-N'-[3-(trimethoxysilyl)propyl]ethylenediamine or analogs thereof with ethoxy rather than methoxy groups, or N-phenyl-, N-cyclohexyl- or N-alkylaminosilanes, mercaptosilanes, epoxysilanes such as, in particular, 3-glycidoxypropyltrimethoxysilane or 3-glycidoxypropyltriethoxysilane, or 3-ureidopropyltrimethoxysilane, (meth)acryloylsilanes, anhydridosilanes, carbamatosilanes, or iminosilanes, adducts of primary aminosilanes with epoxysilanes or (meth)acryloylsilanes or anhydridosilanes, or oligomeric forms of these silanes.

A suitable polymer having silane groups is especially a polyorganosiloxane having terminal silane groups or an organic polymer having silane groups.

A preferred polyorganosiloxane having terminal silane groups has the formula (V)

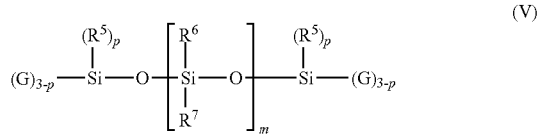

where $R^5$, $R^6$ and $R^7$ are each independently a monovalent hydrocarbyl radical having 1 to 12 carbon atoms, G is a hydroxyl radical or an alkoxy, acetoxy, ketoximato, amido or enoxy radical having 1 to 13 carbon atoms, p is 0, 1 or 2, and m is an integer in the range from 50 to about 2'500.

$R^5$ is preferably methyl, vinyl or phenyl.

$R^6$ and $R^7$ are preferably each independently an alkyl radical having 1 to 5, preferably 1 to 3, carbon atoms, especially methyl.

G is preferably a hydroxyl radical or an alkoxy or ketoximato radical having 1 to 6 carbon atoms, especially a hydroxyl, methoxy, ethoxy, methylethylketoximato or methylisobutylketoximato radical.

More preferably, G is a hydroxyl radical.

p is preferably 0 or 1, especially 0.

In addition, m is preferably selected such that the polyorganosiloxane of the formula (V) has a viscosity at room temperature in the range from 100 to 500'000 mPa·s, especially from 1'000 to 100'000 mPa·s.

Polyorganosiloxanes of the formula (V) are easy to handle and crosslink with moisture and/or silane crosslinkers to give solid silicone polymers having elastic properties.

Suitable commercially available polyorganosiloxanes of the formula (V) are available, for example, from Wacker, Momentive Performance Materials, GE Advanced Materials, Dow Corning, Bluestar Silicones or Shin-Etsu.

A suitable organic polymer having silane groups is especially a polyolefin, polyether, polyester, polyamide, poly(meth)acrylate or mixed forms of these polymers, each bearing one or preferably more than one silane group. The silane groups may be in pendant positions in the chain or in terminal positions and are bonded to the organic polymer via a carbon atom.

More preferably, the organic polymer having silane groups is a polyolefin having silane groups or a polyether having silane groups or a polyester having silane groups or a poly(meth)acrylate having silane groups or a mixed form of these polymers.

Most preferably, the organic polymer having silane groups is a polyether having silane groups.

The silane groups present in the organic polymer having silane groups are preferably alkoxysilane groups, especially alkoxysilane groups of the formula (VI)

where $R^8$ is a linear or branched monovalent hydrocarbyl radical having 1 to 5 carbon atoms, especially methyl, ethyl or isopropyl, $R^9$ is a linear or branched monovalent hydrocarbyl radical having 1 to 8 carbon atoms, especially methyl, and x has a value of 0 or 1 or 2, preferably 0 or 1, especially 0.

More preferably, $R^8$ is methyl or ethyl.

Particular preference is given to trimethoxysilane groups, dimethoxymethylsilane groups or triethoxysilane groups.

Methoxysilane groups have the advantage here that they are particularly reactive and crosslink rapidly, and ethoxysilane groups have the advantage that they are particularly storage-stable and release comparatively nontoxic ethanol in the course of crosslinking.

The organic polymer having silane groups has an average of preferably 1.3 to 4, especially 1.5 to 3, more preferably 1.7 to 2.8, silane groups per molecule. The silane groups are preferably terminal.

The organic polymer having silane groups preferably has an average molecular weight in the range from 1'000 to 30'000 g/mol, especially from 2'000 to 20'000 g/mol.

The organic polymer having silane groups preferably has a silane equivalent weight of 300 to 25'000 g/eq, especially 500 to 15'000 g/eq.

The organic polymer having silane groups may be solid or liquid at room temperature. It is preferably liquid at room temperature.

Most preferably, the organic polymer having silane groups is a polyether having silane groups which is liquid at room temperature, where the silane groups are especially dialkoxysilane groups and/or trialkoxysilane groups, more preferably trimethoxysilane groups or triethoxysilane groups.

Processes for preparing polyethers having silane groups are known to the person skilled in the art.

In a preferred process, polyethers having silane groups are obtainable from the reaction of polyethers containing allyl groups with hydrosilanes, optionally with chain extension using diisocyanates for example.

In a further preferred process, polyethers having silane groups are obtainable from the copolymerization of alkylene oxides and epoxysilanes, optionally with chain extension using diisocyanates for example.

In a further preferred process, polyethers having silane groups are obtainable from the reaction of polyether polyols with isocyanatosilanes, optionally with chain extension using diisocyanates.

In a further preferred process, polyethers having silane groups are obtainable from the reaction of polyethers having isocyanate groups, especially NCO-terminated urethane polyethers from the reaction of polyether polyols with a superstoichiometric amount of polyisocyanates, or with aminosilanes, hydroxysilanes or mercaptosilanes. Polyethers having silane groups from this process are particularly preferred. This process enables the use of a multiplicity of commercially readily available inexpensive starting materials by means of which different polymer properties are obtainable, for example high extensibility, high strength, low modulus of elasticity, low glass transition temperature or high weathering resistance.

It is particularly preferable when the polyether having silane groups is obtainable from the reaction of NCO-terminated urethane polyethers with aminosilanes or hydroxysilanes. Suitable NCO-terminated urethane polyethers are obtainable from the reaction of polyether polyols, especially polyoxyalkylene diols or polyoxyalkylene triols, preferably polyoxypropylene diols or polyoxypropylene triols, with a superstoichiometric amount of polyisocyanates, especially diisocyanates.

It is preferable when the reaction between the polyisocyanate and the polyether polyol is conducted with exclusion of moisture at a temperature of 50° C. to 160° C., optionally in the presence of suitable catalysts, wherein the polyisocyanate has been dosed such that the isocyanate groups thereof are present in a stoichiometric excess in relation to the hydroxyl groups of the polyol. In particular, the excess of polyisocyanate is chosen such that in the resulting urethane polyether, after the reaction of all hydroxyl groups, there remains a content of free isocyanate groups of 0.1% to 5% by weight, preferably 0.2% to 4% by weight, more preferably 0.3% to 3% by weight. Preferred diisocyanates are selected from the group consisting of HDI, IPDI, TDI and MDI. Particular preference is given to IPDI or TDI. Most preferred is IPDI. In this way, polyethers having silane groups with particularly good lightfastness are obtained.

Especially suitable as polyether polyols are polyoxyalkylenediols or polyoxyalkylenetriols having a degree of unsaturation lower than 0.02 meq/g, especially lower than 0.01 meq/g, and an average molecular weight in the range from 400 to 25'000 g/mol, especially 1'000 to 20'000 g/mol.

In addition to polyether polyols it is also possible to use proportions of other polyols, especially polyacrylate polyols and low molecular weight diols or triols.

Suitable aminosilanes for the reaction with an NCO-terminated urethane polyether are primary and secondary aminosilanes. Preference is given to 3-aminopropyltrimethoxysilane, 3-aminopropyldimethoxymethylsilane, 4-aminobutyltrimethoxysilane, 4-amino-3-methylbutyltrimethoxysilane, 4-amino-3,3-dimethylbutyltrimethoxysilane, N-butyl-3-aminopropyltrimethoxysilane, N-phenyl-3-aminopropyltrimethoxysilane, adducts formed from primary aminosilanes such as 3-aminopropyltrimethoxysilane, 3-aminopropyldimethoxymethylsilane or N-(2-aminoethyl)-3-aminopropyltrimethoxysilane and Michael acceptors such as acrylonitrile, (meth)acrylic esters, (meth)acrylamides, maleic or fumaric diesters, citraconic diesters or itaconic diesters, especially dimethyl or diethyl N-(3-trimethoxysilylpropyl)aminosuccinate. Likewise suitable are analogs of the recited aminosilanes with ethoxy or isopropoxy groups in place of the methoxy groups on the silicon.

Suitable hydroxysilanes for the reaction with an NCO-terminated urethane polyether are especially obtainable from the addition of aminosilanes onto lactones or onto cyclic carbonates or onto lactides.

Aminosilanes suitable for this purpose are especially 3-aminopropyltrimethoxysilane, 3-aminopropyltriethoxysilane, 4-aminobutyltrimethoxysilane, 4-aminobutyltriethoxysilane, 4-amino-3-methylbutyltrimethoxysilane, 4-amino-3-methylbutyltriethoxysilane, 4-amino-3,3-dimethylbutyltrimethoxysilane, 4-amino-3,3-dimethylbutyltriethoxysilane, 2-aminoethyltrimethoxysilane or 2-aminoethyltriethoxysilane. Particular preference is given to 3-aminopropyltrimethoxysilane, 3-aminopropyltriethoxysilane, 4-amino-3,3-dimethylbutyltrimethoxysilane or 4-amino-3,3-dimethylbutyltriethoxysilane.

Suitable lactones are especially γ-valerolactone, γ-octalactone, δ-decalactone, and ε-decalactone, especially γ-valerolactone.

Suitable cyclic carbonates are especially 4,5-dimethyl-1,3-dioxolan-2-one, 4,4-dimethyl-1,3-dioxolan-2-one, 4-ethyl-1,3-dioxolan-2-one, 4-methyl-1,3-dioxolan-2-one or 4-(phenoxymethyl)-1,3-dioxolan-2-one.

Suitable lactides are especially 1,4-dioxane-2,5-dione (lactide formed from 2-hydroxyacetic acid, also called "glycolide"), 3,6-dimethyl-1,4-dioxane-2,5-dione (lactide formed from lactic acid, also called "lactide") or 3,6-diphenyl-1,4-dioxane-2,5-dione (lactide formed from mandelic acid).

Preferred hydroxysilanes that are obtained in this way are N-(3-triethoxysilylpropyl)-2-hydroxypropanamide, N-(3-triethoxysilylpropyl)-4-hydroxypentanamide, N-(3-triethoxysilylpropyl)-4-hydroxyoctanamide, N-(3-triethoxysilylpropyl)-5-hydroxydecanamide, N-(3-triethoxysilylpropyl)-2-hydroxypropyl carbamate and the corresponding silanes with methoxy in place of the ethoxy groups.

Suitable hydroxysilanes are additionally also obtainable from the addition of aminosilanes onto epoxides or from the addition of amines onto epoxysilanes. Preferred hydroxysilanes which are obtained in this way are 2-morpholino-4(5)-(2-trimethoxysilylethyl)cyclohexan-1-ol, 2-morpholino-4(5)-(2-triethoxysilyl-ethyl)cyclohexan-1-ol or 1-morpholino-3-(3-(triethoxysilyl)propoxy)propan-2-ol.

Further suitable polyethers having silane groups are commercially available products, especially the following: MS Polymer™ (from Kaneka Corp.; especially the S203H, S303H, S227, S810, MA903 and S943 products); MS Polymer™ or Silyl™ (from Kaneka Corp.; especially the SAT010, SAT030, SAT200, SAX350, SAX400, SAX725, MAX450, MAX951 products); Excestar® (from Asahi Glass Co. Ltd.; especially the S2410, S2420, S3430, S3630 products); SPUR+* (from Momentive Performance Materials; especially the 1010LM, 1015LM, 1050MM products); Vorasil™ (from Dow Chemical Co.; especially the 602 and 604 products); Desmoseal® (from Covestro AG; especially the S XP 2458, S XP 2636, S XP 2749, S XP 2774 and S XP 2821 products), TEGOPAC® (from Evonik Industries AG; especially the Seal 100, Bond 150, Bond 250 products), Polymer HBZ (from Hanse Chemie AG/Evonik Industries AG, especially the 47, 48, 61, 61LV, 77, 80, 81 products); Geniosil® STP (from Wacker Chemie AG; especially the E10, E15, E30, E35 products).

Particularly preferred organic polymers having silane groups have end groups of the formula (VII)

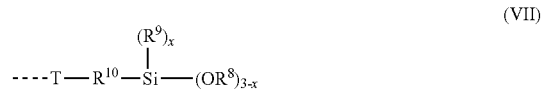

where $R^{10}$ is a divalent linear or branched hydrocarbyl radical which has 1 to 12 carbon atoms and optionally has cyclic and/or aromatic moieties and optionally one or more heteroatoms, especially one or more nitrogen atoms, T is a divalent radical selected from —O—, —S—, —N($R^{11}$)—, —O—CO—N($R^{11}$)—, —N($R^{11}$)—CO—O— and —N($R^{11}$)—CO—N($R^{11}$)—, where $R^{11}$ is a hydrogen radical or a linear or branched hydrocarbyl radical having 1 to 20 carbon atoms which optionally has cyclic moieties and which optionally has an alkoxysilane, ether or carboxylic ester group, and $R^8$, $R^9$ and x are as defined above.

It is preferable when $R^{10}$ is 1,3-propylene or 1,4-butylene, wherein butylene may be substituted by one or two methyl groups.

It is particularly preferable when $R^{10}$ is 1,3-propylene.

The invention further provides a curable composition comprising at least one amidine containing at least one structural unit of the formula (I) as described above. In this case, the amidine catalyzes the crosslinking or curing of the composition.

Preferably, the curable composition contains reactive groups selected from silane groups, isocyanate groups, epoxy groups and cyanate ester groups.

More preferably, the curable composition contains silane groups and/or isocyanate groups, especially silane groups.

Preferably, the curable composition comprises at least one polyisocyanate or at least one polyurethane polymer having isocyanate groups or at least one silane or at least one polymer having silane groups, as described above.

More preferably, the curable composition comprises at least one silane and/or at least one polymer having silane groups.

Preferably, the curable composition is used for bonding, sealing, insulating, coating or pretreating in construction and industrial applications, especially as concrete element adhesive, facade adhesive, parquet adhesive, window profile adhesive, anchoring adhesive, assembly adhesive, bodywork adhesive, pane adhesive, sandwich element adhesive, lining adhesive, laminate adhesive, packaging adhesive, joint sealant, floor grout, spackling compound, sealing membrane, weld or crimp seam sealant, cavity seal, building foam, furniture foam, filter foam, insulation foam, sound insulation foam, packaging foam, bodywork foam, floor covering, floor coating, balcony coating, roof coating, concrete protection coating, parking garage coating, pipe coating, anticorrosion coating, textile coating, primer, activator or primer coat, or as molding, semifinished product, film or fiber, especially as cushioning, pillow, mattress, shoe sole, shock absorber, damping element, gasket, tire, roll, bearing, drum, conveyor belt, hose, housing, window profile, insulation panel, model construction panel, sandwich element, fiber composite body, implant, packaging film, lamination film or textile fiber.

In particular, the curable composition is an adhesive or a sealant or a coating.

Most preferably, the curable composition comprises at least one polymer having silane groups, especially selected from the group consisting of polyorganosiloxanes having terminal silane groups and organic polymers having silane groups, as described above.

A composition of this kind has good storage stability with no propensity to separation, and because of the low toxicity and low volatility of the amidine containing at least one structural unit of the formula (I) allows a low hazard classification and enables low-emissions and largely odorless products that cure rapidly and at the same time form a mechanically high-quality and durable material. A particularly advantageous circumstance here is that this material shows barely any propensity to migration-related defects such as exudation or substrate soiling, by contrast with compositions comprising catalysts according to the prior art, for example DBU or TMG. Compositions comprising such catalysts known from the prior art have a propensity to migration effects, which can be manifested prior to curing by separation and after curing by tacky and/or greasy surfaces and/or substrate soiling. Particularly the latter effects are extremely undesirable, since tacky and greasy surfaces are rapidly soiled and are difficult to paint over, and substrate contaminants can lead to lasting discoloration.

A curable composition comprising a polyorganosiloxane having terminal silane groups has the advantage that it is particularly water- and light-stable and enables particularly flexible properties.

A curable composition comprising an organic polymer having silane groups has the advantage of having particularly good adhesion properties on a multitude of substrates and being particularly inexpensive.

Preferably, a composition comprising a polyorganosiloxane having terminal silane groups, especially a polyorganosiloxane of the formula (V), additionally comprises at least one silane crosslinker, especially a silane of the formula (VIII)

where $R^{12}$ is a monovalent hydrocarbyl radical having 1 to 12 carbon atoms,

G' is a hydroxyl radical or is an alkoxy, acetoxy, ketoximato, amido or enoxy radical having 1 to 13 carbon atoms, and q has a value of 0, 1 or 2, especially 0 or 1.

Particularly suitable silanes of the formula (VIII) are methyltrimethoxysilane, ethyltrimethoxysilane, propyltrimethoxysilane, octyltrimethoxysilane, isooctyltrimethoxysilane, vinyltrimethoxysilane, phenyltrimethoxysilane, methyltriethoxysilane, octyltriethoxysilane, isooctyltriethoxysilane, vinyltriethoxysilane, phenyltriethoxysilane, tetramethoxysilane, tetraethoxysilane, methyltris(methylethylketoximo)silane, vinyltris(methylethylketoximo)silane or methyltris(isobutylketoximo)silane.

Preferably, the amidine containing at least one structural unit of the formula (I) is present in the curable composition in such an amount that the concentration of amidine groups based on the amount of the functional compound, especially based on the amount of the polymer having silane groups, is in the range from 0.1 to 50 mmol/100 g, preferably 0.2 to 50 mmol/100 g, especially 0.5 to 20 mmol/100 g.

Such a composition has good storability and rapid curing.

In addition to the amidine containing at least one structural unit of the formula (I), the composition may comprise further catalysts which especially catalyze the crosslinking of isocyanate groups and/or silane groups. Suitable further catalysts are especially metal compounds and/or basic nitrogen or phosphorus compounds.

Suitable metal compounds are especially compounds of tin, titanium, zirconium, aluminum or zinc, especially diorganotin(IV) compounds such as in particular dibutyltin(IV) diacetate, dibutyltin(IV) dilaurate, dibutyltin(IV) dineodecanoate or dibutyltin(IV) bis(acetylacetonate) and dioctyltin (IV) dilaurate and also titanium(IV) or zirconium(IV) or aluminum(II) or zinc(II) complexes having in particular alkoxy, carboxylate, 1,3-diketonate, 1,3-ketoesterate or 1,3-ketoamidate ligands.

Suitable basic nitrogen or phosphorus compounds are especially imidazoles, pyridines, phosphazene bases or preferably amines, hexahydrotriazines, biguanides, guanidines or further amidines.

Suitable amines are, in particular, alkyl-, cycloalkyl- or aralkylamines such as triethylamine, triisopropylamine, 1-butylamine, 2-butylamine, tert-butylamine, 3-methyl-1-butylamine, 3-methyl-2-butylamine, dibutylamine, tributylamine, hexylamine, dihexylamine, cyclohexylamine, dicyclohexylamine, dimethylcyclohexylamine, benzylamine, dibenzylamine, dimethylbenzylamine, octylamine, 2-ethylhexylamine, di-(2-ethylhexyl)amine, laurylamine, N,N-dimethyllaurylamine, stearylamine, N,N-dimethylstearylamine; fatty amines derived from natural fatty acid mixtures; aliphatic, cycloaliphatic or araliphatic diamines such as ethylenediamine, butanediamine, hexamethylenediamine, dodecanediamine, neopentanediamine, 2-methylpentamethylenediamine (MPMD), 2,2(4),4-trimethylhexamethylenediamine (TMD), isophoronediamine (IPD), 2,5(2,6)-bis(aminomethyl)bicyclo[2.2.1]heptane (NBDA), xylylene-1,3-diamine (MXDA), N,N'-di(tert-butyl)ethylenediamine, N,N,N',N'-tetramethylethylenediamine, N,N,N',N'-tetramethylpropylenediamine, N,N,N',N'-tetramethylhexamethylenediamine, 3-(dimethylamino)propylamine, 3-(methylamino)propylamine, 3-(cyclohexylamino)propylamine, piperazine, N-methylpiperazine, N,N'-dimethylpiperazine, 1,4-diazabicyclo[2.2.2]octane (DABCO), fatty polyamines such as N-cocoalkylpropane-1,3-diamine; polyalkyleneamines such as diethylenetriamine, dipropylenetriamine, triethylenetetramine (TETA), tetraethylenepentamine (TEPA), pentamethylenehexamine (PEHA), 3-(2-aminoethyl)aminopropylamine, N,N'-bis(3-aminopropyl)ethylenediamine, N-(3-aminopropyl)-N-methylpropanediamine, bis(3-dimethylaminopropyl)amine, N-(3-dimethylaminopropyl)propylene-1,3-diamine, N-(2-aminoethyl)piperazine (N-AEP), N-(2-aminopropyl)piperazine, N,N'-di-(2-aminoethyl)piperazine, 1-methyl-4-(2-dimethylaminoethyl)piperazine, N,N,N',N'',N''-pentamethyldiethylenetriamine, N,N,N',N'',N''-pentamethyldipropylenetriamine, polyethyleneimines obtainable for example under the trade names Lupasol® (from BASF) and Epomin® (from Nippon Shokubai); ether amines, such as, in particular, 2-methoxyethylamine, 2-ethoxyethylamine, 3-methoxypropylamine, 3-ethoxypropylamine, 3-(2-ethylhexyloxy)propylamine, 3-(2-methoxyethoxy)propylamine, morpholine, N-methylmorpholine, N-ethylmorpholine, 2-aminoethylmorpholine, bis(2-aminoethyl) ether, bis(dimethylaminoethyl) ether, bis(morpholinoethyl) ether (DMDEE), N,N,N'-trimethyl-N'-hydroxyethyl-bis(2-aminoethyl) ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine, or 2-aminopropyl-terminated glycols, of the kind obtainable for example under the trade name Jeffamine® (from Huntsman); amino alcohols, such as, in particular, ethanolamine, isopropanolamine, diethanolamine, diisopropanolamine, triethanolamine, triisopropanolamine, N-butylethanolamine, diglycolamine, N,N-diethylethanolamine, N-methyldiethanolamine, N-methyldiisopropylamine, N,N,N'-trimethylaminoethylethanolamine, N-(3-dimethylaminopropyl)-N,N-diisopropanolamine, N,N-bis(3-dimethylaminopropyl)-N-isopropanolamine, 2-(2-dimethylaminoethoxy)ethanolamine, or adducts of mono- and polyamines with epoxides or diepoxides; amines containing phenol groups, such as, in particular, condensation products of phenols, aldehydes, and amines (called Mannich bases and phenalkamines) such as, in particular, 2-(dimethylaminomethyl)phenol, 2,4,6-tris(dimethylaminomethyl)phenol, or polymers of phenol, formaldehyde, and N,N-dimethylpropane-1,3-diamine, and also phenalkamines obtainable commercially under the brand names Cardolite® (from Cardolite), Aradur® (from Huntsman), and Beckopox® (from Cytec); polyamines containing amide groups, so-called polyamidoamines, of the kind available commercially, for example, under the brand names Versamid® (from Cognis), Aradur® (from Huntsman), Euretek® (from Huntsman) or Beckopox® (from Cytec); or aminosilanes, such as, in particular, 3-aminopropyltrimethoxysilane, 3-aminopropyldimethoxymethylsilane, N-(2-aminoethyl)-3-aminopropyltrimethoxysilane, N-(2-aminoethyl)-3-aminopropylmethyldimethoxysilane, N-(2-aminoethyl)-N'-[3-(trimethoxysilyl)propyl]ethylenediamine or their analogs with ethoxy in place of the methoxy groups on the silicon atom.

Suitable hexahydrotriazines are especially 1,3,5-hexahydrotriazine, 1,3,5-trimethylhexahydrotriazine or 1,3,5-tris (3-(dimethylamino)propyl)hexahydrotriazine.

Suitable biguanides are especially biguanide, 1-butylbiguanide, 1,1-dimethylbiguanide, 1-butylbiguanide, 1-phenylbiguanide or 1-(o-tolyl)biguanide (OTBG).

Suitable guanidines are especially 1-butylguanidine, 1,1-dimethylguanidine, 1,3-dimethylguanidine, 1,1,3,3-tetramethylguanidine (TMG), 2-(3-(trimethoxysilyl)propyl)-1,1,3,3-tetramethylguanidine, 2-(3-(methyldimethoxysilyl)propyl)-1,1,3,3-tetramethylguanidine, 2-(3-(triethoxysilyl)propyl)-1,1,3,3-tetramethylguanidine, 1,5,7-triazabicyclo[4.4.0]dec-5-ene (TBD), 7-methyl-1,5,7-triazabicyclo[4.4.0]dec-5-ene, 7-cyclohexyl-1,5,7-triazabicyclo[4.4.0]dec-5-ene, 1-phenylguanidine, 1-(o-tolyl)guanidine (OTG), 1,3-diphenylguanidine, 1,3-di(o-tolyl)guanidine or 2-guanidinobenzimidazole.

Suitable further amidines are especially 1,8-diazabicyclo[5.4.0]undec-7-ene (DBU), 1,5-diazabicyclo[4.3.0]non-5-ene (DBN), 6-dibutylamino-1,8-diazabicyclo[5.4.0]undec-7-ene, 6-dibutylamino-1,8-diazabicyclo[5.4.0]undec-7-ene, N,N'-di-n-hexylacetamidine (DHA), 2-methyl-1,4,5,6-tetrahydropyrimidine, 1,2-dimethyl-1,4,5,6-tetrahydropyrimidine, 2,5,5-trimethyl-1,4,5,6-tetrahydropyrimidine, N-(3-trimethoxysilylpropyl)-4,5-dihydroimidazole or N-(3-triethoxysilylpropyl)-4,5-dihydroimidazole.

In addition, the composition may comprise, as cocatalyst, an acid, especially a carboxylic acid. Preference is given to aliphatic carboxylic acids such as formic acid, lauric acid, stearic acid, isostearic acid, oleic acid, 2-ethyl-2,5-dimethylcaproic acid, 2-ethylhexanoic acid, neodecanoic acid, fatty acid mixtures from the hydrolysis of natural fats and oils or di- and polycarboxylic acids, especially poly(meth)acrylic acids.

In a preferred embodiment, the composition is essentially free of organotin compounds. Organotin-free compositions are advantageous in terms of protection of health and protection of the environment. More particularly, the tin content of the curable composition is less than 0.1% by weight, especially less than 0.05% by weight.

In a further preferred embodiment, the composition comprises a combination of at least one amidine containing at least one structural unit of the formula (I) and at least one organotin compound, especially a diorganotin(IV) compound such as those mentioned above. Such a composition has a high curing rate even in the case of a low tin content, which is advantageous for toxicological and environmental reasons.

In one embodiment, the composition additionally comprises, as well as the amidine containing at least one structural unit of the formula (I), at least one organotitanate. A combination of the amidine containing at least one structural unit of the formula (I) and an organotitanate has particularly high catalytic activity. This enables rapid curing with a comparatively small use amount of organotitanate.

Suitable organotitanates are especially titanium(IV) complexes.

Preferred organotitanates are especially selected from
   titanium(IV) complexes having two 1,3-diketonate ligands, especially 2,4-pentanedionate (=acetylacetonate), and two alkoxide ligands;
   titanium(IV) complexes having two 1,3-ketoesterate ligands, especially ethylacetoacetate, and two alkoxide ligands;

titanium(IV) complexes having one or more aminoalkoxide ligands, especially triethanolamine or 2-((2-aminoethyl)amino)ethanol, and one or more alkoxide ligands;

titanium(IV) complexes having four alkoxide ligands (orthotitanates);

and more highly condensed organotitanates, especially oligomeric titanium(IV) tetrabutoxide, also referred to as polybutyl titanate;

where suitable alkoxide ligands are especially isobutoxy, n-butoxy, isopropoxy, ethoxy and 2-ethylhexoxy.

Especially suitable are the commercially available products Tyzor® AA, GBA, GBO, AA-75, AA-65, AA-105, DC, BEAT, BTP, TE, TnBT, KTM, TOT, TPT or IBAY (all from Dorf Ketal); Tytan PBT, TET, X85, TAA, ET, S2, S4 or S6 (all from Borica Company Ltd.) and Ken-React® KR® TTS, 7, 9QS, 12, 26S, 33DS, 38S, 39DS, 44, 134S, 138S, 133DS, 158FS or LICA® 44 (all from Kenrich Petrochemicals).

Very particularly suitable organotitanates are selected from bis(ethylaceto-acetato)diisobutoxytitanium(IV) (commercially available, for example, as Tyzor® IBAY from Dorf Ketal), bis(ethylacetoacetato)diisopropoxytitanium (IV) (commercially available, for example, as Tyzor® DC from Dorf Ketal), bis(acetylacetonato)diisopropoxytitanium (IV), bis(acetylacetonato)diisobutoxytitanium(IV), tris(oxyethyl)amineisopropoxytitanium(IV), bis[tris(oxyethyl)amine]diisopropoxytitanium(IV), bis(2-ethylhexane-1,3-dioxy)titanium(IV), tris[2-((2-aminoethyl)amino)ethoxy]ethoxytitanium(IV), bis(neopentyl(diallyl)oxy)diethoxytitanium(IV), tetra(isopropoxy)titanate, tetra(n-butoxy)titanate, tetra(2-ethylhexyloxy)titanate and polybutyl titanate.

Most preferred are bis(ethylacetoacetato)diisobutoxytitanium(IV) or bis(ethylacetoacetato)diisopropoxytitanium (IV).

The curable composition preferably comprises at least one further constituent selected from the group consisting of fillers, plasticizers, rheology additives, desiccants, adhesion promoters and crosslinkers. More preferably, it comprises any combination of two or more of these constituents.

Suitable fillers are especially inorganic or organic fillers, especially natural, ground or precipitated calcium carbonates, optionally coated with fatty acids, especially stearic acid, baryte (heavy spar), talcs, quartz flours, quartz sand, dolomites, wollastonites, kaolins, calcined kaolins, mica (potassium aluminum silicate), molecular sieves, aluminum oxides, aluminum hydroxides, magnesium hydroxide, silicas including finely divided silicas from pyrolysis processes, industrially produced carbon blacks, graphite, metal powders such as aluminum, copper, iron, silver or steel, PVC powder or hollow spheres.

Suitable plasticizers are especially trialkylsilyl-terminated polydialkylsiloxanes, preferably trimethylsilyl-terminated polydimethylsiloxanes, especially having viscosities in the range from 10 to 1'000 mPa·s, or corresponding compounds in which some of the methyl groups have been replaced by other organic groups, especially phenyl, vinyl or trifluoropropyl groups, called reactive plasticizers, in the form of monofunctional polysiloxanes, i.e. those that are reactive at one end, carboxylic esters such as phthalates, especially dioctyl phthalate, bis(2-ethylhexyl) phthalate, bis (3-propylheptyl) phthalate, diisononyl phthalate or diisodecyl phthalate, diesters of ortho-cyclohexane-dicarboxylic acid, especially diisononyl 1,2-cyclohexanedicarboxylate, adipates, especially dioctyl adipate, bis(2-ethylhexyl) adipate, azelates, especially bis(2-ethylhexyl) azelate, sebacates, especially bis(2-ethylhexyl) sebacate or diisononyl sebacate, polyols, especially polyoxyalkylene polyols or polyester polyols, glycol ethers, glycol esters, organic phosphoric or sulfonic esters, sulfonamides, polybutenes, or fatty acid methyl or ethyl esters derived from natural fats or oils, also called "biodiesel", plasticizers containing siloxane groups being particularly suitable for polymers having silane groups in the form of polyorganosiloxanes.

Suitable rheology additives are especially thickeners, especially sheet silicates such as bentonites, derivatives of castor oil, hydrogenated castor oil, polyamides, polyurethanes, urea compounds, fumed silicas, cellulose ethers or hydrophobically modified polyoxyethylenes.

Suitable desiccants are especially tetraethoxysilane, vinyltrimethoxysilane, vinyltriethoxysilane or organoalkoxysilanes which have a functional group in the a position to the silane group, especially N-(methyldimethoxysilylmethyl)-O-methylcarbamate, (methacryloyloxymethyl)silanes, methoxymethylsilanes, orthoformic esters, calcium oxide, molecular sieves, highly reactive isocyanates such as p-tosyl isocyanate, monomeric diisocyanates or monooxazolidines such as Incozol® 2 (from Incorez), especially vinyltrimethoxysilane or vinyltriethoxysilane.

Suitable adhesion promoters and/or crosslinkers are especially aminosilanes such as, in particular, 3-aminopropyltrimethoxysilane, 3-aminopropyldimethoxymethylsilane, N-(2-aminoethyl)-3-aminopropyltrimethoxysilane, N-(2-aminoethyl)-3-aminopropyldimethoxymethylsilane, N-(2-aminoethyl)-N'-[3-(trimethoxysilyl)propyl]ethylenediamine or the analogs thereof with ethoxy in place of methoxy groups, and also N-phenyl-, N-cyclohexyl- or N-alkylaminosilanes, mercaptosilanes, epoxysilanes, (meth)acrylosilanes, anhydridosilanes, carbamatosilanes, alkylsilanes or iminosilanes, oligomeric forms of these silanes, adducts formed from primary aminosilanes with epoxysilanes or (meth)acrylosilanes or anhydridosilanes, amino-functional alkylsilsesquioxanes, especially amino-functional methylsilsesquioxane or amino-functional propylsilsesquioxane. Especially suitable are 3-aminopropyltrimethoxysilane, 3-aminopropyltriethoxysilane, N-(2-aminoethyl)-3-aminopropyltrimethoxysilane, N-(2-aminoethyl)-3-aminopropyltriethoxysilane, 3-glycidoxypropyltrimethoxysilane, 3-glycidoxypropyltriethoxysilane or 3-ureidopropyltrimethoxysilane, or oligomeric forms of these silanes.

In a preferred embodiment, the composition comprises at least one desiccant and at least one adhesion promoter and/or crosslinker.

In a preferred embodiment, the composition does not comprise any phthalates as plasticizers. Such compositions are toxicologically advantageous and in some cases have fewer problems with migration effects.

If the composition comprises a polyisocyanate and/or a polyurethane polymer having isocyanate groups, additionally preferably, at least one polyfunctional compound reactive toward isocyanate groups is present, such as, in particular, one or more polyols, especially the polyols mentioned as being suitable for the preparation of a polyurethane polymer having isocyanate groups. Preference is given to polyether polyols, polyester polyols, polycarbonate polyols, poly(meth)acrylate polyols or polybutadiene polyols. Particular preference is given to polyether polyols, especially polyoxypropylene polyols and/or ethylene oxide-terminated polyoxypropylene polyols. Preference is given to polyols having an average molecular weight in the range from 400 to 10'000 g/mol, especially 500 to 6'000 g/mol. Preference is given to polyols having an average OH functionality in the range from 1.6 to 4, especially 1.8 to 3, more preferably 2.2 to 3. Likewise suitable are polyether polyols with polymer particles dispersed therein, especially those with styrene-acrylonitrile particles (SAN) or polyurea or polyhydrazodicarbonamide particles (PHD).

chain extenders, especially ethane-1,2-diol, propane-1,3-diol, 2-methylpropane-1,3-diol, butane-1,4-diol, pentane-1,5-diol, neopentyl glycol, hexane-1,6-diol, 3-methylpentane-1,5-diol, heptane-1,7-diol, octane-1,8-diol, cyclohexane-1,3-dimethanol, cyclohexane-1,4-dimethanol, diethylene glycol or triethylene glycol;

amino alcohols, especially 2-aminoethanol, 2-(2-aminoethoxy)ethanol or 3-aminomethyl-3,5,5-trimethylcyclohexanol or derivatives thereof that have ether, ester or urethane groups;

compounds having blocked amino groups, especially aldimines, ketimines, enamines, oxazolidines, imidazolidines or hexahydropyrimidines;

or polyamines.

The composition may contain further constituents, especially the following auxiliaries and admixtures:

pigments, especially titanium dioxide or iron oxides;

dyes;

stabilizers against oxidation, heat, light or UV radiation;

natural resins, fats or oils such as rosin, shellac, linseed oil, castor oil or soya oil;

non-reactive polymers such as, in particular, homo- or copolymers of unsaturated monomers, especially from the group comprising ethylene, propylene, butylene, isobutylene, isoprene, vinyl acetate or alkyl (meth) acrylates, especially polyethylenes (PE), polypropylenes (PP), polyisobutylenes, ethylene-vinyl acetate copolymers (EVA) or atactic poly-α-olefins (APAO);

flame-retardant substances, especially the already mentioned fillers aluminum hydroxide and magnesium hydroxide, or, in particular, organic phosphoric esters such as, in particular, triethyl phosphate, tricresyl phosphate, triphenyl phosphate, diphenyl cresyl phosphate, isodecyl diphenyl phosphate, tris(1,3-dichloro-2-propyl) phosphate, tris(2-chloroethyl) phosphate, tris(2-ethylhexyl) phosphate, tris(chloroisopropyl) phosphate, tris(chloropropyl) phosphate, isopropylated triphenyl phosphate, mono-, bis- or tris(isopropylphenyl) phosphates of different degrees of isopropylation, resorcinol bis(diphenyl phosphate), bisphenol A bis(diphenyl phosphate) or ammonium polyphosphates;

fibers, especially glass fibers, carbon fibers, metal fibers, ceramic fibers or polymer fibers such as polyamide fibers or polyethylene fibers;

surface-active substances, especially wetting agents, leveling agents, deaerating agents or defoamers;

solvents;

biocides, especially algicides, fungicides or substances that inhibit fungal growth;

and other substances customarily used in curable compositions.

It may be advisable to subject certain constituents to chemical or physical drying before mixing them into the composition.

The composition is preferably produced and stored under exclusion of moisture. It is typically storage-stable with exclusion of moisture in a suitable package or arrangement, such as, in particular, a cartridge, a bottle, a canister, a pouch, a bucket, a hobbock or a vat.

The composition may be in the form of a one-component composition or in the form of a multi-component, especially two-component, composition.

In the present document, "one-component" refers to a composition in which all constituents of the composition are stored in a mixture in the same container and which is curable with moisture.

In the present document, "two-component" refers to a composition in which the constituents of the composition are present in two different components which are stored in separate containers. Only shortly before or during the application of the composition are the two components mixed with one another, whereupon the mixed composition cures, optionally under the action of moisture.

If the composition comprises a polyisocyanate and/or a polyurethane polymer having isocyanate groups, it is preferably a two-component composition. In this case, one component contains the polyisocyanate and/or the polyurethane polymer having isocyanate groups and the other component contains the amidine containing at least one structural unit of the formula (I) and additionally at least one polyfunctional compound reactive toward isocyanate groups.

If the composition comprises an organic polymer having silane groups, it is preferably a one-component composition.

If the composition comprises a polyorganosiloxane having terminal silane groups, it is preferably a one-component composition, also referred to as RTV-1, or a two-component composition, also referred to as RTV-2. In the case of an RTV-2 composition, the polyorganosiloxane having terminal silane groups is preferably a constituent of the first component, and a silane crosslinker, especially a silane of the formula (VIII), is preferably a constituent of the second component. The amidine containing at least one structural unit of the formula (I) may be present here in the first and/or in the second component.

Any second or optionally further components is/are mixed with the first component prior to or during application, especially by means of a static mixer or by means of a dynamic mixer.

The composition is especially applied at ambient temperature, preferably within a temperature range between 0° C. and 45° C., especially 5° C. to 35° C., and also cures under these conditions.

On application, the crosslinking reaction of the functional groups commences, if appropriate under the influence of moisture.

Isocyanate groups present react with hydroxyl groups, or primary or secondary amino groups, or under the influence of moisture with blocked amino groups.

Any further isocyanate groups present react with one another under the influence of moisture.

Silane groups present can condense with silanol groups present to afford siloxane groups (Si—O—Si groups). Silane groups present can also be hydrolyzed on contact with moisture to give silanol groups (Si—OH groups) and can form siloxane groups (Si—O—Si groups) through subsequent condensation reactions.

As a result of these reactions, the composition ultimately cures. The amidine containing at least one structural unit of the formula (I) accelerates this curing.

If water is required for the curing, this can either come from the air (atmospheric humidity), or else the composition can be contacted with a water-containing component, for example by painting, for example with a smoothing agent, or by spraying, or water or a water-containing component can be added to the composition on application, for example in the form of a water-containing or water-releasing liquid or paste. A paste is especially suitable if the composition itself is in the form of a paste.

In the case of curing by means of atmospheric humidity, the composition cures from the outside inward, at first forming a skin on the surface of the composition. The so-called skin time is a measure of the curing rate of the composition. The speed of curing is generally determined by various factors, for example the availability of water, the temperature, etc.

The composition is suitable for a multitude of uses, especially as a paint, varnish or primer, as a resin for production of fiber composites, as a rigid foam, flexible foam, molding, elastomer, fiber, film or membrane, as a potting compound, sealant, adhesive, covering, coating or paint for construction and industrial applications, for example as a seam seal, cavity seal, electrical insulation compound, spackling compound, joint sealant, weld or crimp seam sealant, assembly adhesive, bodywork adhesive, glazing adhesive, sandwich element adhesive, lining adhesive, laminate adhesive, packaging adhesive, wood adhesive, parquet adhesive, anchoring adhesive, floor covering, floor coating, balcony coating, roof coating, concrete protection coating, parking garage coating, seal, pipe coating, anticorrosion coating, textile coating, damping element, sealing element or spackling compound.

The composition is particularly suitable as an adhesive and/or sealant, especially for joint sealing and for elastic adhesive bonds in construction and industrial applications, or as elastic coating with crack-bridging properties, especially for protection and/or sealing of, for example, roofs, floors, balconies, parking decks or concrete pipes.

The composition is thus preferably an adhesive or a sealant or a coating.

A composition of this kind typically comprises fillers, plasticizers, desiccants, adhesion promoters and/or cross-linkers and optionally further auxiliaries and additives.

For use as an adhesive or sealant the composition preferably has a pasty consistency with pseudoplastic properties. A pasty sealant or adhesive of this kind is especially applied to a substrate from standard cartridges which are operated manually, with compressed air or with a battery, or from a vat or hobbock via a delivery pump or an extruder, optionally via an application robot. For use as a coating the composition preferably has a liquid consistency at room temperature with self-leveling properties. It may be slightly thixotropic, such that the coating is applicable to inclined to vertical surfaces without flowing away immediately. It is especially applied by means of a roller or brush or by pouring-out and distribution by means, for example, of a roller, a scraper or a notched trowel.

During application the composition is preferably applied to at least one substrate.

Suitable substrates are especially
- glass, glass ceramic, concrete, mortar, brick, tile, gypsum and natural rocks such as limestone, granite or marble;
- metals and alloys such as aluminum, iron, steel or non-ferrous metals, and also surface-finished metals or alloys such as galvanized or chromed metals;
- leather, textiles, paper, wood, wood-based materials bonded with resins, for example phenolic, melamine or epoxy resins, resin-textile composites and further polymer composites;
- plastics such as polyvinyl chloride (rigid and flexible PVC), acrylonitrile-butadiene-styrene copolymers (ABS), polycarbonate (PC), polyamide (PA), polyesters, poly(methyl methacrylate) (PMMA), epoxy resins, polyurethanes (PUR), polyoxymethylene (POM), polyolefins (PO), polyethylene (PE) or polypropylene (PP), ethylene/propylene copolymers (EPM) and ethylene/propylene/diene terpolymers (EPDM), and fiber-reinforced plastics such as carbon fiber-reinforced composite plastics (CFP), glass fiber-reinforced plastics (GFP) and sheet molding compounds (SMC), where the plastics may preferably have been surface-treated by means of plasma, corona or flames;
- coated substrates such as powder-coated metals;
- paints or varnishes, especially automotive topcoats, metal paints, furniture varnishes or wood varnishes.

If required, the substrates can be pretreated prior to the application of the composition, especially by physical and/or chemical cleaning methods or by the application of an adhesion promoter, an adhesion promoter solution or a primer.

The composition is particularly suitable for contact with substrates that are particularly sensitive to defects caused by migrating substances, especially by the formation of discoloration or specks. These are, in particular, fine-pore substrates such as marble, limestone or other natural stones, gypsum, cement mortar or concrete, but also plastics. Especially on PVC, severe discoloration is observed in the presence of catalysts, for example DBU or TMG, and cannot be removed by cleaning. No such effects are observed with the amidine containing at least one structural unit of the formula (I).

It is possible to bond or seal two identical or two different substrates, especially the aforementioned substrates.

After the curing of the composition, a cured composition is obtained.

The invention thus further provides a cured composition obtained from the curable composition described.

The use of the composition affords an article which has in particular been bonded, sealed or coated with the composition. The article is especially a built structure, especially a structure built by structural engineering or civil engineering, an industrially manufactured item or a consumable item, especially a window, a domestic appliance or a means of transport such as in particular an automobile, a bus, a truck, a rail vehicle, a ship, an aircraft or a helicopter; or the article may be an installable component thereof.

The curable composition is storable and applicable in a pleasant manner due to low odor. After application, it builds up strength surprisingly quickly, giving rise to mechanically high-quality and stable materials. The composition does not have a tendency to migration-related defects such as separation, exudation or substrate soiling either before or after curing.

EXAMPLES

Working examples are adduced hereinafter, which are intended to elucidate the invention described in detail. It will be appreciated that the invention is not restricted to these described working examples.

"Standard climatic conditions" refer to a temperature of 23±1° C. and a relative air humidity of 50±5%.

Unless stated otherwise, the chemicals used were from Sigma-Aldrich.

$^1$H NMR spectra were measured on a spectrometer of the Bruker Ascend 400 type at 400.14 MHz; the chemical shifts δ are reported in ppm relative to tetramethylsilane (TMS). No distinction was made between true coupling and pseudo-coupling patterns.

Infrared spectra (FT-IR) were measured on a Nicolet iS5 FT-IR instrument from Thermo Scientific equipped with a horizontal ATR measurement unit with a diamond crystal. Liquid samples were applied undiluted as films; solid samples were dissolved in $CH_2Cl_2$. The absorption bands are reported in wavenumbers ($cm^{-1}$) (measurement window: 4000-650 $cm^{-1}$).

The skin time (HBZ) was determined by applying a few grams of the composition to cardboard in a film thickness of about 2 mm and measuring under standard climatic conditions the time until, upon gentle tapping of the surface of the composition using an LDPE pipette, no residue remained on the pipette for the first time.

The characteristics of the surface were tested by touch.

The mechanical properties of tensile strength, elongation at break and modulus of elasticity (at 0-5% and 0-50% elongation) were measured in accordance with DIN EN 53504 at a pulling speed of 200 mm/min.

Viscosity was measured on a thermostated Rheotec RC30 cone-plate viscometer (cone diameter 50 mm, cone angle 1°, cone tip-plate distance 0.05 mm, shear rate 10 rpm).

Preparation of Compounds of the Formula (IV)

N,N-Diethyl(2-oxocyclopentyl)carbonamide

N,N-Diethyl(2-oxocyclopentyl)carbonamide was prepared by reacting methyl 2-oxocyclopentanecarboxylate with diethylamine with removal of methanol and subsequent purification by means of distillation. What was obtained was a pale yellowish liquid having a boiling temperature of 110° C. at 0.1 mbar.

FT-IR: 2967, 2933, 2877, 1737, 1628, 1447, 1431, 1380, 1361, 1327, 1262, 1219, 1139, 1099, 1003, 973, 921, 835, 820, 786, 682.

N,N-Dibutyl(2-oxocyclopentyl)carbonamide

N,N-Dibutyl(2-oxocyclopentyl)carbonamide was prepared by reacting methyl 2-oxocyclopentanecarboxylate with dibutylamine with removal of methanol and subsequent purification by means of distillation. What was obtained was a pale yellowish liquid having a boiling temperature of 130° C. at 0.1 mbar.

FT-IR: 2957, 2931, 2872, 1740, 1671, 1634, 1564, 1445, 1427, 1373, 1295, 1253, 1181, 1140, 1104, 1053, 1003, 928, 903, 834, 767, 732.

Preparation of Amidines

Amidine A1: 5-(1-(3-dimethylaminopropyl)-1,4,5,6-tetrahydropyrimidin-2-yl)-N,N-diethylpentanamide To an initial charge of 17.6 g (0.11 mol) of 3-(3-(dimethylamino)propylamino)propylamine (from BASF) in 30 mL of toluene in a round-bottom flask were slowly added dropwise, while stirring and cooling, 20.3 g (0.11 mol) of N,N-diethyl(2-oxocyclopentyl)carbonamide, prepared as described above. The reaction mixture was stirred at 40° C. overnight. Subsequently, the azeotrope of toluene and water was distilled off at 40° C. and mbar. Then the mixture was heated to 135 to 140° C. at standard pressure and the rest of the toluene was removed by distillation. After cooling to room temperature, 32.5 g of product were obtained as a pale orange, odorless, low-viscosity liquid.

$^1$H-NMR ($CDCl_3$): 1.03 and 1.07 (2×t, 6H, J=7.1 Hz, N($CH_2CH_3$)$_2$), 1.55 to 1.64 (m, 6H, $CH_2CH_2CH_2CH_2CO$ and $CH_2CH_2CH_2N(CH_3)_2$), 1.72 (p, 2H, CH=NCH$_2$CH$_2$CH$_2$N), 2.14 (s, 6H, N(CH$_3$)$_2$), 2.17 (m, 4H, N=CHCH$_2$ and CH$_2$CO), 2.26 (m, 2H, CH$_2$N(CH$_3$)$_2$), 3.09 and 3.25 (q and m, 10H, CH=NCH$_2$CH$_2$CH$_2$NCH$_2$CH$_2$CH$_2$N(CH$_3$)$_2$ and N(CH$_2$CH$_3$)$_2$).

FT-IR: 2966, 2932, 2856, 2815, 2763, 1639, 1614, 1458, 1444, 1423, 1377, 1362, 1316, 1260, 1223, 1151, 1131, 1096, 2082, 1069, 1039, 974, 945, 870, 842, 792, 763.

Amidine A2: 5-(1-(3-dimethylaminopropyl)-1,4,5,6-tetrahydropyrimidin-2-yl)-N,N-dibutylpentanamide To an initial charge of 19.3 g (0.12 mol) of 3-(3-(dimethylamino)propylamino)propylamine (from BASF) in 30 mL of toluene in a round-bottom flask were slowly added dropwise, while stirring and cooling, 29.9 g (0.12 mol) of N,N-dibutyl(2-oxocyclopentyl)carbonamide, prepared as described above. The reaction mixture was stirred at 40° C. overnight. Subsequently, the azeotrope of toluene and water was distilled off at 40° C. and mbar. Then the mixture was heated to 145 to 150° C. at standard pressure and the rest of the toluene was removed by distillation. After cooling to room temperature, 39.7 g of product were obtained as an orange, odorless, low-viscosity liquid.

$^1$H-NMR ($CDCl_3$): 0.86 and 0.89 (2×t, 6H, J=7.1 Hz, N(CH$_2$CH$_2$CH$_2$CH$_3$)$_2$), 1.23 (m, 4H, N(CH$_2$CH$_2$CH$_2$CH$_3$)$_2$), 1.43 (m, 4H, N(CH$_2$CH$_2$CH$_2$CH$_3$)$_2$), 1.60 (m, 6H, CH$_2$CH$_2$CH$_2$CH$_2$CO and CH$_2$CH$_2$CH$_2$N(CH$_3$)$_2$), 1.73 (m, 2H, CH=NCH$_2$CH$_2$CH$_2$N), 2.13 (s, 6H, N(CH$_3$)$_2$), 2.17 (m, 4H, N=CHCH$_2$ and CH$_2$CO), 2.25 (m, 2H, CH$_2$N(CH$_3$)$_2$), 3.10 and 3.24 (q and m, 10H, CH=NCH$_2$CH$_2$CH$_2$NCH$_2$CH$_2$CH$_2$N(CH$_3$)$_2$ and N(CH$_2$CH$_2$CH$_2$CH$_3$)$_2$).

FT-IR: 2953, 2930, 2859, 2715, 2763, 1640, 1613, 1565, 1457, 1420, 1369, 1317, 1290, 1259, 1209, 1132, 1114, 1098, 1040, 974, 930, 869, 821, 785, 766, 732.

Amidine A3: 5-(1-methyl-1,4,5,6-tetrahydropyrimidin-2-yl)-N,N-dibutylpentanamide To an initial charge of 8.8 g (0.10 mol) of N-methylpropane-1,3-diamine in 50 mL of toluene in a round-bottom flask were slowly added dropwise, while stirring and cooling, 23.9 g (0.10 mol) of N,N-dibutyl(2-oxocyclopentyl)carbonamide, prepared as described above. The reaction mixture was stirred at 40° C. for 3 hours. Subsequently, the azeotrope of toluene and water was distilled off at 40 to 50° C. and 1 mbar. Then the mixture was heated gradually to 150° C. at standard pressure and the rest of the toluene was removed by distillation. After cooling to room temperature, 27.6 g of product were obtained as an orange, odorless, low-viscosity liquid.

$^1$H-NMR ($CDCl_3$): 0.86 (m, 6H, N(CH$_2$CH$_2$CH$_2$CH$_3$)$_2$), 1.23 (m, 4H, N(CH$_2$CH$_2$CH$_2$CH$_3$)$_2$), 1.43 (m, 4H, N(CH$_2$CH$_2$CH$_2$CH$_3$)$_2$), 1.59 (m, 4H, CH$_2$CH$_2$CH$_2$CH$_2$CO), 1.74 (m, 2H, CH=NCH$_2$CH$_2$CH$_2$N), 2.20 and 2.26 (2×m, 4H, N=CHCH$_2$ and CH$_2$CO), 2.81 (s, 3H, N—CH$_3$), 3.06 and 3.13 (2×m, 4H, NCH$_2$CH$_2$CH$_2$N), 3.23 (m, 4H, N(CH$_2$CH$_2$CH$_2$CH$_3$)$_2$).

FT-IR: 2954, 2928, 2871, 2860, 1741, 1635, 1650, 1563, 1455, 1422, 1400, 1370, 1306, 1255, 1210, 1131, 1098, 1068, 1040, 954, 930, 903, 732.

Amidine A4: 5-(1-cocoalkyl-1,4,5,6-tetrahydropyrimidin-2-yl)-N,N-dibutylpentanamide Amidine A4 was prepared as described for amidine A3, except using 25.7 g (0.10 mol) of N-cocoalkylpropane-1,3- diamine (Duomeen CD from Akzo Nobel) in place of N-methylpropane-1,3-diamine. After cooling to room temperature, 46.4 g of product were obtained as an orange, odorless, low-viscosity liquid.

$^1$H-NMR (CDCl$_3$): 0.86 (m, 9H, N(CH$_2$CH$_2$CH$_2$CH$_3$)$_2$ and alkyl chain-CH$_3$), 1.22 (s br, 22H, N(CH$_2$CH$_2$CH$_2$CH$_3$)$_2$ and (CH$_2$)$_9$), 1.47 (m, 6H, N(CH$_2$CH$_2$CH$_2$CH$_3$)$_2$ and NCH$_2$CH$_2$-alkyl chain), 1.60 (m, 4H, CH$_2$CH$_2$CH$_2$CH$_2$CO), 1.74 (m, 2H, CH=NCH$_2$CH$_2$CH$_2$N), 2.18 and 2.28 (2×m, 4H, N=CHCH$_2$ and CH$_2$CO), 3.10 (m, 6H, NCH$_2$CH$_2$N and NCH$_2$-alkyl chain), 3.26 (m, 4H, N(CH$_2$CH$_2$CH$_3$)$_2$).

FT-IR: 2955, 2922, 2852, 1643, 1615, 1566, 1464, 1455, 1419, 1370, 1317, 1288, 1265, 1207, 1130, 1100, 961, 930, 886, 765, 722.

Amidine A5: 5-(1,4,5,6-tetrahydropyrimidin-2-yl)-N,N-dibutylpentanamide

Amidine A5 was prepared as described for amidine A3, except using 7.4 g (0.12 mol) of propane-1,3-diamine in place of N-methylpropane-1,3-diamine. After cooling to room temperature, 25.7 g of product were obtained as an orange, odorless, low-viscosity liquid.

$^1$H-NMR (CDCl$_3$): 0.86 (m, 6H, N(CH$_2$CH$_2$CH$_2$CH$_3$)$_2$), 1.23 (m, 4H, N(CH$_2$CH$_2$CH$_2$CH$_3$)$_2$), 1.43 (m, 4H, N(CH$_2$CH$_2$CH$_2$CH$_3$)$_2$), 1.57 (m, 4H, CH$_2$CH$_2$CH$_2$CH$_2$CO), 1.67 (m, 2H, CH=NCH$_2$CH$_2$CH$_2$N), 2.05 and 2.25 (2×m, 4H, N=CHCH$_2$ and CH$_2$CO), 3.12 (m, 4H, NCH$_2$CH$_2$CH$_2$N), 3.23 (m, 4H, N(CH$_2$CH$_2$CH$_2$CH$_3$)$_2$).

FT-IR: 3331, 3215, 2955, 2929, 2860, 1742, 1631, 1537, 1454, 1424, 1366, 1316, 1289, 1259, 1205, 1138, 1103, 1061, 980, 929, 902, 882, 837, 799, 732.

Amidine A6: methyl 5-(1-methyl-1,4,5,6-tetrahydropyrimidin-2-yl)pentanecarboxylate Amidine A6 was prepared as described for amidine A3, except using 14.2 g (0.10 mol) of methyl 2-oxocyclopentanecarboxylate in place of N,N-dibutyl(2-oxocyclopentyl)carbonamide. After cooling to room temperature, 19.7 g of product were obtained as a dark-colored, odorless, low-viscosity liquid.

$^1$H-NMR (CDCl$_3$): 1.61 (m, 4H, CH$_2$CH$_2$CH$_2$CH$_2$CO), 1.74 (m, 2H, CH=NCH$_2$CH$_2$CH$_2$N), 2.18 and 2.26 (2×m, 4H, N=CHCH$_2$ and CH$_2$CO), 2.80 (s, 3H, N—CH$_3$), 3.06 and 3.23 (2×m, 4H, NCH$_2$CH$_2$CH$_2$N), 3.59 (m, 3H, OCH$_3$).

FT-IR: 3313, 3025, 2944, 2850, 2801, 1731, 1660, 1601, 1567, 1544, 1498, 1461, 1435, 1390, 1306, 1269, 1239, 1185, 1140, 1035, 1110, 1054, 1030, 917, 892, 844, 774, 728, 694.

Amidine A7: Reaction Mixture Comprising N,N'-((1,1,3,3-tetramethyldisiloxane-1,3-diyl)bis(propane-3,1-diyl))bis(5-(1-methyl-1,4,5,6-tetrahydropyrimidin-2-yl)pentanamide To an initial charge of 7.6 g (0.036 mol) of amidine A6, prepared as described above, in a round-bottom flask were added, while stirring, 4.5 g (0.018 mol) of bis(3-aminopropyl)-1,1,3,3-tetramethyldisiloxane, and the mixture was heated gradually up to 160° C. under reduced pressure. After cooling to room temperature, 9.8 g of a dark-colored, odorless, low-viscosity liquid were obtained.

FT-IR: 3307, 2926, 2861, 1737, 1645, 1605, 1549, 1437, 1403, 1364, 1309, 1250, 1185, 1137, 1040, 837, 792, 774, 698.

Amidine R1: 1-(3-dimethylaminopropyl)-2-methyl-1,4,5,6-tetrahydropyrimidine

To an initial charge of 131.6 g of ethyl acetoacetate in 50 mL of toluene in a round-bottom flask were slowly added dropwise, while stirring and cooling, 161.1 g of 3-(3-(dimethylamino)propylamino)propylamine (from BASF), while keeping the temperature at 20 to 30° C. The reaction mixture was stirred at 40° C. overnight. Thereafter, the azeotrope of toluene and water was removed from the reaction mixture by means of distillation at 40° C. and 10 mbar, and then the rest of the toluene and ethyl acetate was removed by means of distillation at standard pressure and the residue was distilled under reduced pressure. 168.7 g of product were obtained as a yellowish, odorless, low-viscosity liquid having a boiling temperature of 95 to 105° C. at 0.6 mbar.

Amidines A1 to A7 are amidines having structural units of the formula (I). Amidine R1 is a comparative example.

Preparation of Polyethers Having Silane Groups:
Polymer STP-1:

With exclusion of moisture, 1000 g of Acclaim® 12200 polyol (polyoxypropylenediol having a low level of unsaturation, from Covestro; OH number 11.0 mg KOH/g), 43.6 g of isophorone diisocyanate (IPDI; Vestanat® IPDI, from Evonik), 126.4 g of diisononyl cyclohexane-1,2-dicarboxylate (DINCH) and 0.1 g of bismuth tris(neodecanoate) (10% by weight in DINCH) were heated up to 90° C. while stirring constantly and left at this temperature until the content of free isocyanate groups determined by titrimetry had reached a stable value of 0.63% by weight. Subsequently, 63.0 g of diethyl N-(3-trimethoxysilylpropyl)aminosuccinate (adduct of 3-aminopropyltrimethoxysilane and diethyl maleate; prepared as per U.S. Pat. No. 5,364,955) were mixed in and the mixture was stirred at 90° C. until it was no longer possible to detect any free isocyanate by FT-IR spectroscopy. The polyether having trimethoxysilane groups obtained in this way was cooled down to room temperature and stored with exclusion of moisture.

Polymer STP-2:

With exclusion of moisture, 1000 g of Acclaim® 12200 polyol (polyoxypropylenediol having a low level of unsaturation, from Covestro; OH number 11.0 mg KOH/g), 43.6 g of isophorone diisocyanate (IPDI; Vestanat® IPDI, from Evonik), 126.4 g of diisononyl cyclohexane-1,2-dicarboxylate (DINCH) and 0.1 g of bismuth tris(neodecanoate) (10% by weight in DINCH) were heated up to 90° C. while stirring constantly and left at this temperature until the content of free isocyanate groups determined by titrimetry had reached a stable value of 0.64% by weight. Subsequently, 70.6 g of diethyl N-(3-triethoxysilylpropyl)-aminosuccinate (adduct formed from 3-aminopropyltriethoxysilane and diethyl maleate) were mixed in and the mixture was stirred at 90° C. until it was no longer possible to detect any free isocyanate by means of FT-IR spectroscopy. The polyether having triethoxysilane groups obtained in this way was cooled down to room temperature and stored with exclusion of moisture.

Commercial Catalysts Used:
DBU 1,8-diazabicyclo[5.4.0]undec-7-ene (Lupragen® N 700, from BASF)

Compositions Based on Polymers Having Silane Groups:

Comparative examples in tables 1 to 4 are indicated by "(Ref)".

Compositions Z1 to Z9:

A composition composed of 97.6 g of polymer STP-1, 2.0 g of vinyltrimethoxysilane and 0.4 g of 3-aminopropyltrimethoxysilane was blended with various catalysts in the amount specified according to table 1, and the mixture was tested for viscosity at 25° C. and skin time (HBZ) under standard climatic conditions, before and after storage. Skin time serves as a measure of the activity of the catalyst in relation to the crosslinking reaction of the silane groups, i.e. of the crosslinking rate; the change in viscosity and the skin time after storage are a measure of storage stability of the composition. In addition, the mixture applied, after 24 h under standard climatic conditions, was tested as to whether the surface was dry as desired or whether a greasy film had formed, which is a sign of the exudation of the catalyst owing to poor compatibility with the cured polymer, and/or whether the surface was tacky, which is a sign of incomplete curing. In addition, the mixture was used to produce a film of thickness 2 mm, which was cured under standard climatic conditions for 7 days and tested for mechanical properties.

The results are shown in tables 1 and 2.

TABLE 1

| Compo- | | | | Viscosity [Pa · s] | | HBZ | |
|---|---|---|---|---|---|---|---|
| sition | Catalyst | Amount | Concentration[1] | fresh | stored[2] | fresh | stored[2] |
| Z1 (Ref) | Amidine R1 | 0.34 g | 1.9 | 21.3 | 22.2 | 31' | 32' |
| Z2 (Ref) | DBU | 0.30 g | 1.9 | 26.3 | 31.0 | 29' | 31' |
| Z3 | Amidine A1 | 0.63 g | 1.9 | 24.9 | 41.2 | 25' | 25' |
| Z4 | Amidine A2 | 0.74 g | 1.9 | 24.5 | 41.9 | 25' | 25' |
| Z5 | Amidine A3 | 0.60 g | 1.9 | 46.5 | 49.3 | 36' | 27' |
| Z6 | Amidine A4 | 0.93 g | 1.9 | 44.5 | 47.0 | 35' | 30' |
| Z7 | Amidine A5 | 0.58 g | 1.9 | 46.2 | 48.7 | 25' | 21' |
| Z8 | Amidine A6 | 0.41 g | 1.9 | 34.1 | 37.7 | 38' | 40' |
| Z9 | Amidine A7 | 0.59 g | 1.9 | 27.9 | 31.1 | 33' | 40' |

[1]mmol of amidine groups per 100 g of polyether having silane groups.
[2]for 7 days at 70° C. in a closed container.

TABLE 2

| | Surface | Tensile | Elongation | Modulus of elasticity | |
|---|---|---|---|---|---|
| Composition | after 24 h | strength | at break | 0-5% | 0-50% |
| Z1 (Ref) | slightly tacky | 0.62 MPa | 78% | 1.2 MPa | 0.8 MPa |
| Z2 (Ref) | greasy | 0.70 MPa | 95% | 1.0 MPa | 0.8 MPa |
| Z3 | dry | 0.69 MPa | 83% | 1.2 MPa | 0.8 MPa |
| Z4 | dry | 0.63 MPa | 72% | 1.2 MPa | 0.8 MPa |
| Z5 | dry | 0.71 MPa | 88% | 1.3 MPa | 0.8 MPa |
| Z6 | dry | 0.65 MPa | 84% | 1.2 MPa | 0.8 MPa |
| Z7 | dry | 0.65 MPa | 85% | 1.2 MPa | 0.8 MPa |
| Z8 | dry | 0.80 MPa | 108% | 1.2 MPa | 0.8 MPa |
| Z9 | dry | 0.79 MPa | 111% | 1.2 MPa | 0.8 MPa |

Compositions Z10 to Z15:

In a planetary mixer, 36.2 g of polymer STP-2, 60.2 g of ground chalk (Omyacarb® 5 GU, from Omya), 1.2 g of thixotropic paste, the preparation of which is described hereinafter, 1.2 g of vinyltriethoxysilane, 1.2 g of 3-aminopropyltriethoxysilane and various catalysts in the amount specified according to table 3 were blended, and the mixture was tested as described for composition Z1 for viscosity, skin time (HBZ), surface characteristics and mechanical properties. The results are shown in tables 3 and 4.

The thixotropic paste was prepared by gently heating an initial charge of 300 g of diisodecyl phthalate (Palatinol® Z, from BASF) and 48 g of 4,4'-methylene diphenyl diisocyanate (Desmodur® 44 MC L, from Covestro) in a vacuum mixer and then slowly adding 27 g of n-butylamine dropwise while stirring vigorously. The resultant paste was stirred for a further hour under reduced pressure while cooling.

TABLE 3

| Compo- | | | Concen- | Viscosity [Pa · s] | | HBZ | |
|---|---|---|---|---|---|---|---|
| sition | Catalyst | Amount | tration[1] | fresh | stored[2] | fresh | stored[2] |
| Z10 (Ref) | DBU | 0.40 g | 2.6 | n.d. | n.d. | 1 h 23' | n.d. |
| Z11 | Amidine A1 | 0.84 g | 2.6 | 109 | 183 | 2 h 45' | 5 h |
| Z12 | Amidine A2 | 0.99 g | 2.6 | 105 | 179 | 3 h | 2 h |
| Z13 | Amidine A3 | 0.81 g | 2.6 | 139 | 167 | 4 h | 5 h |
| Z14 | Amidine A4 | 1.24 g | 2.6 | 130 | 154 | 3 h 55' | 3 h 30' |
| Z15 | Amidine A5 | 0.77 g | 2.6 | 157 | 175 | 3 h 55' | 3 h |

[1]mmol of amidine groups per 100 g of composition.
[2]for 7 days at 70° C. in a closed container.
"n.d." stands for "not determined"

TABLE 4

| | Surface | Tensile | Elongation | Modulus of elasticity | |
|---|---|---|---|---|---|
| Composition | after 24 h | strength | at break | 0-5% | 0-50% |
| Z10 (Ref) | greasy | 2.5 MPa | 155% | 4.0 MPa | 2.0 MPa |
| Z11 | dry | 2.5 MPa | 141% | 4.4 MPa | 2.7 MPa |
| Z12 | dry | 2.3 MPa | 133% | 4.1 MPa | 2.5 MPa |
| Z13 | dry | 1.8 MPa | 143% | 3.2 MPa | 1.9 |
| Z14 | dry | 1.9 MPa | 137% | 3.6 MPa | 2.1 |
| Z15 | dry | 1.9 MPa | 155% | 3.7 MPa | 2.1 |

The invention claimed is:

1. An amidine containing at least one structural unit of the formula (I)

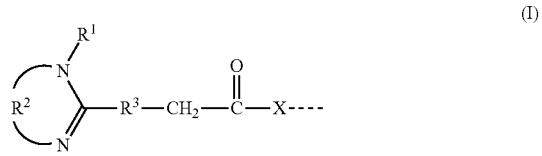

(I)

where
R[1] is a hydrogen radical or an alkyl, cycloalkyl or aralkyl radical optionally having unsaturated moieties, having 1 to 30 carbon atoms and optionally having a tertiary amino group,
R[2] is an optionally alkyl-substituted 1,2-ethylene or 1,3-propylene radical, R³ is an optionally alkyl-substituted 1,3-propylene or 1,4-butylene radical, and X is O or NR⁴ where R⁴ is a hydrogen radical or is an alkyl, cycloalkyl or aralkyl radical having 1 to 8 carbon atoms.

2. The amidine as claimed in claim 1, wherein R¹ is selected from the group consisting of methyl, ethyl, propyl, butyl, cyclohexyl, 2-ethylhexyl, n-decyl, lauryl, cocoalkyl, oleyl, soyaalkyl, tallowalkyl and 3-(N,N-dimethylamino)propyl.

3. The amidine as claimed in claim 1, wherein X is NR⁴.

4. The amidine as claimed in claim 1, wherein the amidine has the formula (II)

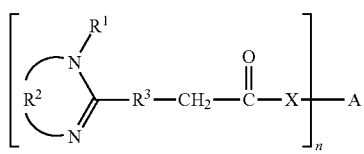
(II)

where n is 1 or 2 or 3, and

A is an n-valent radical which has a molecular weight in the range from 28 to 5,000 g/mol and is bonded via carbon atoms.

5. The amidine as claimed in claim 4, wherein A is a monovalent hydrocarbyl radical which has 1 to 30 carbon atoms and optionally contains ether oxygen or tertiary amine nitrogen or siloxane units.

6. The amidine as claimed in claim 4, wherein A is a di- or trivalent hydrocarbyl radical which has 2 to 50 carbon atoms and optionally contains ether oxygen or tertiary amine nitrogen or siloxane units.

7. A process for preparing the amidine of the formula (II) as claimed in claim 4, wherein at least one amine of the formula (III) is reacted with a compound of the formula (IV) with removal of water

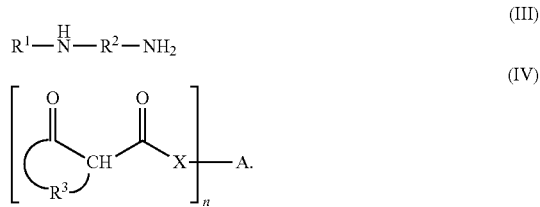

8. The process as claimed in claim 7, wherein a compound of the formula (IV) with X=NR⁴ is used, which has been obtained beforehand by reacting at least one amine of the formula A-(NHR⁴)ₙ with a compound of the formula (IV) with X=O with removal of the corresponding alcohol.

9. A method comprising applying the amidine as claimed in claim 1 as catalyst for the crosslinking of a functional compound.

10. The method as claimed in claim 9, wherein the functional compound is a silane, a polymer having silane groups, a polyisocyanate or a polyurethane polymer having isocyanate groups.

11. A curable composition comprising at least one amidine as claimed in claim 1.

12. The curable composition as claimed in claim 11, further comprising at least one functional compound having at least one silane group and/or isocyanate groups.

13. The curable composition as claimed in claim 11, further comprising at least one polymer having silane groups.

14. The curable composition as claimed in claim 11, wherein the curable composition is an adhesive or a sealant or a coating.

15. A cured composition obtained from the curable composition as claimed in claim 11.

* * * * *